(12) United States Patent
Nishimura et al.

(10) Patent No.: US 10,135,000 B2
(45) Date of Patent: Nov. 20, 2018

(54) ORGANIC ELECTROLUMINESCENT ELEMENT AND ELECTRONIC DEVICE

(71) Applicant: IDEMITSU KOSAN CO., LTD., Tokyo (JP)

(72) Inventors: Kazuki Nishimura, Sodegaura (JP); Hiroyuki Saito, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 175 days.

(21) Appl. No.: 15/128,806

(22) PCT Filed: Mar. 25, 2015

(86) PCT No.: PCT/JP2015/059154
§ 371 (c)(1),
(2) Date: Sep. 23, 2016

(87) PCT Pub. No.: WO2015/151965
PCT Pub. Date: Oct. 8, 2015

(65) Prior Publication Data
US 2017/0110667 A1    Apr. 20, 2017

(30) Foreign Application Priority Data

Mar. 31, 2014  (JP) .................... 2014-072905

(51) Int. Cl.
| | |
|---|---|
| *H01L 51/00* | (2006.01) |
| *C09K 11/06* | (2006.01) |
| *C09K 11/02* | (2006.01) |
| *C07C 13/66* | (2006.01) |
| *H01L 51/50* | (2006.01) |
| *H05B 33/14* | (2006.01) |

(52) U.S. Cl.
CPC .......... *H01L 51/0058* (2013.01); *C07C 13/66* (2013.01); *C09K 11/025* (2013.01); *C09K 11/06* (2013.01); *H01L 51/006* (2013.01); *H01L 51/0052* (2013.01); *H01L 51/0054* (2013.01); *H01L 51/0061* (2013.01); *H01L 51/0073* (2013.01); *H01L 51/5004* (2013.01); *H01L 51/5024* (2013.01); *H05B 33/14* (2013.01); *C07C 2603/40* (2017.05); *C09K 2211/1007* (2013.01); *C09K 2211/1011* (2013.01); *C09K 2211/1014* (2013.01); *C09K 2211/1022* (2013.01); *C09K 2211/1088* (2013.01); *H01L 51/5016* (2013.01); *H01L 51/5028* (2013.01); *H01L 51/5056* (2013.01); *H01L 51/5072* (2013.01)

(58) Field of Classification Search
CPC .................. C09K 11/025; C09K 11/06; C09K 2211/1007; C09K 2211/1011; C09K 2211/1014; C09K 2211/1022; C09K 2211/1088; C09K /; H01L 51/0052; H01L 51/0054; H01L 51/0058; H01L 51/006; H01L 51/0061; H01L 51/0073; H01L 51/5016; H01L 51/5028; H01L 51/5056
See application file for complete search history.

(56) References Cited

FOREIGN PATENT DOCUMENTS

| | | |
|---|---|---|
| JP | 2001-284050 A | 10/2001 |
| JP | 2005-240008 A | 9/2005 |
| JP | 2006-032883 A | 2/2006 |
| JP | 2006-128632 A | 5/2006 |
| JP | 2008-294404 A | 12/2008 |
| JP | 2009-188136 A | 8/2009 |
| JP | 2010-245061 A | 10/2010 |
| JP | 2012-022953 A | 2/2012 |
| JP | 2012-099593 A | 5/2012 |
| JP | 2013-135237 A | 7/2013 |
| JP | 5669163 B1 | 2/2015 |
| KR | 10-2011-0053568 A | 5/2011 |
| WO | WO-2006/059512 A1 | 6/2006 |
| WO | WO-2008/143791 A1 | 11/2008 |
| WO | WO-2010/134352 A1 | 11/2010 |
| WO | WO-2010/143434 A1 | 12/2010 |
| WO | WO-2012/070233 A1 | 5/2012 |
| WO | WO-2012/070234 A1 | 5/2012 |
| WO | WO-2014/034891 A1 | 3/2014 |

OTHER PUBLICATIONS

Machine translation for JP 2005-240008 A (publication date: Sep. 2005).*
Tanaka et al., "Twisted Intramolecular Charge Transfer State for Long-Wavelength Thermally Activated Delayed Fluorescence," Sep. 2, 2013.
English-Language Translation of International Search Report issued in International Patent Application No. PCT/JP2015/059154 dated Jun. 16, 2015.

* cited by examiner

Primary Examiner — Dawn L Garrett
(74) Attorney, Agent, or Firm — Foley & Lardner LLP

(57) ABSTRACT

An organic electroluminescence device includes an anode, a cathode, and an emitting layer, in which the emitting layer contains a first compound, a second compound, and a third compound, a singlet energy $S(M1)$ of the first compound and a singlet energy $S(M2)$ of the second compound satisfy a numerical formula (Numerical Formula 1) below, an electron affinity $Af(M1)$ of the first compound and an electron affinity $Af(M2)$ of the second compound satisfy a numerical formula (Numerical Formula 2) below, and a triplet energy $T(M1)$ of the first compound satisfies a numerical formula (Numerical Formula 3) below, $S(M2) \geq S(M1) \times 0.95$    (Numerical Formula 1)

$Af(M2) - Af(M1) \geq 0.2 eV$    (Numerical Formula 2)

$T(M1) \leq 2.0 eV$    (Numerical Formula 3).

27 Claims, 1 Drawing Sheet

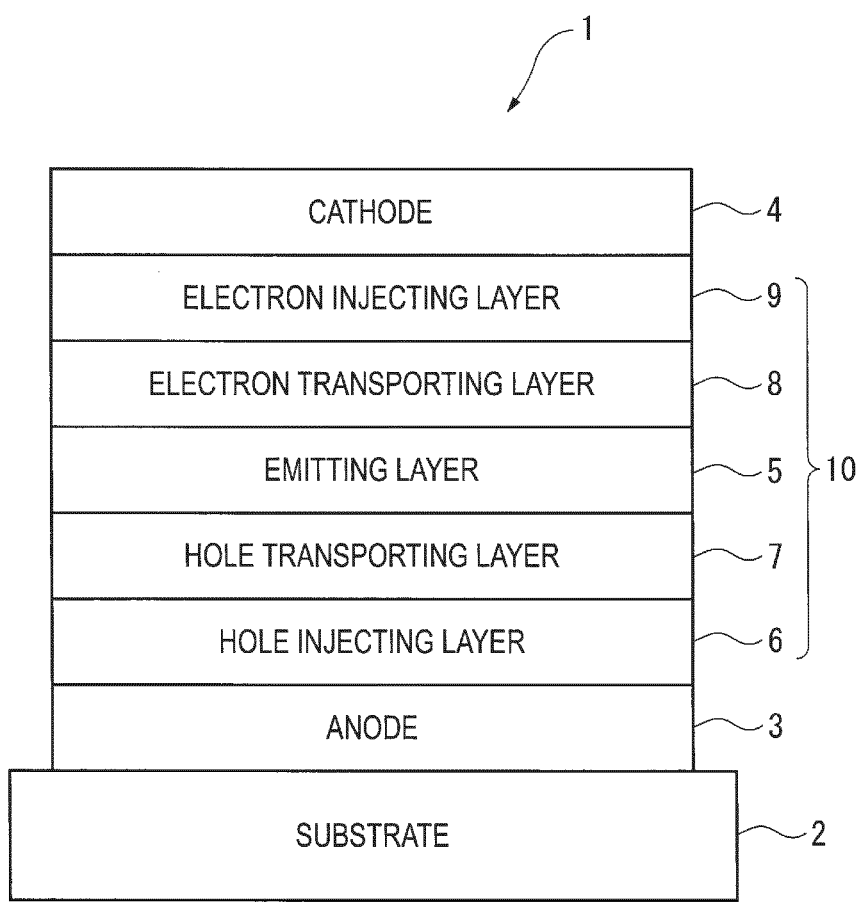

ORGANIC ELECTROLUMINESCENT ELEMENT AND ELECTRONIC DEVICE

CROSS-REFERENCE TO RELATED APPLICATIONS

The present application is a U.S. national stage application claiming the benefit of International Patent Application No. PCT/JP2015/059154, filed Mar. 25, 2015, which claims the benefit of priority to Japanese Patent Application No. 2014-072905, filed Mar. 31, 2014, the entireties of which are hereby incorporated by reference.

TECHNICAL FIELD

The present invention relates to an organic electroluminescence device and an electronic device.

BACKGROUND ART

An organic electroluminescence device (hereinafter, occasionally abbreviated as organic EL device) using an organic substance is highly expected to be used as an inexpensive solid-emitting full-color display device having a large area and has been variously developed. A typical organic EL device includes an emitting layer and a pair of opposing electrodes between which the emitting layer is interposed. When an electric field is applied on both of the electrodes, electrons are injected from the cathode while holes are injected from the anode. Further, the electrons are recombined with the holes in the emitting layer to generate an excited state. When the excited state is returned to a ground state, energy is emitted as light.

The emitting layer typically contains the host material and the dopant material, where excitation is caused by the host material and light is emitted by the dopant material. Such separation of the functions of the host material and the dopant material promotes development of technology of improving a device performance.

For instance, Patent Literatures 1 to 4 disclose an organic electrical field light emission device including an organic emitting layer in which a host material, a hole-trapping dopant, and an electron-trapping dopant coexist. In the organic electrical field light emission device disclosed in Patent Literature 1, the holes injected into the organic emitting layer are trapped by the hole-trapping dopant while the electrons injected into the organic emitting layer are trapped by the electron-trapping dopant.

In the organic electrical field light emission device disclosed in Patent Literatures 1 to 3, both of the hole-trapping dopant and the electron-trapping dopant have a smaller singlet energy than the host material. In other words, in the organic electrical field light emission device disclosed in Patent Literatures 1 to 3, both of the hole-trapping dopant and the electron-trapping dopant emit light. Accordingly, the light emitted from the organic electrical field light emission device is in a color mixed with emission colors from the respective dopants and has a wide half bandwidth of an emission peak.

Moreover, in Patent Literature 4, both of the host and the hole-trapping dopant have a smaller singlet energy than the electron-trapping dopant. In other words, the hole-trapping dopant emits light. Moreover, the host is a pyrene derivative.

Recently, a further longer lifetime has been desired for a practical use of the organic EL device.

CITATION LIST

Patent Literatures

Patent Literature 1: International Publication No. WO2006/059512
Patent Literature 2: Korean Patent Publication No. 10-2011-0053568
Patent Literature 3: JP-A-2013-135237
Patent Literature 4: JP-A-2008-294404

SUMMARY OF THE INVENTION

Problems to be Solved by the Invention

An object of the invention is to provide an organic electroluminescence device configured to emit light with a long lifetime and an electronic device including the organic electroluminescence device.

Means for Solving the Problems

According to an aspect of the invention, an organic electroluminescence device includes an anode, a cathode, and an emitting layer, in which the emitting layer contains a first compound, a second compound, and a third compound, a singlet energy $S(M1)$ of the first compound and a singlet energy $S(M2)$ of the second compound satisfy a numerical formula (Numerical Formula 1) below, an electron affinity $Af(M1)$ of the first compound and an electron affinity $Af(M2)$ of the second compound satisfy a numerical formula (Numerical Formula 2) below, and a triplet energy $T(M1)$ of the first compound satisfies a numerical formula (Numerical Formula 3) below.

$$S(M2) \geq S(M1) \times 0.95 \quad \text{(Numerical Formula 1)}$$

$$Af(M2) - Af(M1) \geq 0.2 \text{ eV} \quad \text{(Numerical Formula 2)}$$

$$T(M1) \leq 2.0 \text{ eV} \quad \text{(Numerical Formula 3)}.$$

According to another aspect of the invention, an electronic device including the organic electroluminescence device according to the above aspect of the invention is provided.

Accordingly, the organic EL device according to the above aspect of the invention can emit light with a long lifetime. Moreover, according to the another aspect of the invention, the electronic device including the above organic electroluminescence device is provided.

BRIEF DESCRIPTION OF DRAWINGS

The FIGURE shows an outline structure of an organic electroluminescence device according to an exemplary embodiment of the invention.

DESCRIPTION OF EMBODIMENT(S)

First Exemplary Embodiment
In a first exemplary embodiment, an organic EL device includes: a cathode; an anode; and an organic layer provided between the cathode and the anode. The organic layer is configured to have a single layer or a plurality of layers.

In the organic EL device according to the first exemplary embodiment, at least one layer of the organic layer is an emitting layer. Accordingly, the organic layer may be provided by a single emitting layer. Alternatively, the organic layer may be provided by layers applied in a known organic EL device such as a hole injecting layer, a hole transporting layer, an electron injecting layer, an electron transporting layer, a hole blocking layer and an electron blocking layer. The organic layer may include an inorganic compound.

Typical device arrangements of an organic EL device include the following arrangements (a) to (e) and the like:
 (a) anode/emitting layer/cathode;
 (b) anode/hole injecting•transporting layer/emitting layer/cathode;
 (c) anode/emitting layer/electron injecting•transporting layer/cathode;
 (d) anode/hole injecting•transporting layer/emitting layer/electron injecting•transporting layer/cathode; and
 (e) anode/hole injecting•transporting layer/emitting layer/blocking layer/electron injecting•transporting layer/cathode.

While the arrangement (d) is preferably used among the above arrangements, the arrangement of the invention is not limited to the above arrangements.

It should be noted that the above-described "emitting layer" is an organic layer having an emission function.

The "hole injecting•transporting layer (or hole injecting•transporting layer)" means "at least one of a hole injecting layer and a hole transporting layer" while the "electron injecting/ transporting layer (or electron injecting•transporting layer)" means "at least one of an electron injecting layer and an electron transporting layer." Herein, when the hole injecting layer and the hole transporting layer are provided, the hole injecting layer is preferably between the hole transporting layer and the anode. When the electron injecting layer and the electron transporting layer are provided, the electron injecting layer is preferably closer to the cathode.

The FIGURE schematically shows an arrangement of the organic EL device according to the first exemplary embodiment.

An organic EL device 1 shown in the FIGURE includes a substrate 2, an anode 3, a cathode 4 and an organic layer 10 disposed between the anode 3 and the cathode 4.

The organic layer 10 includes a hole injecting layer 6, hole transporting layer 7, emitting layer 5, electron transporting layer 8, and electron injecting layer 9 which are sequentially laminated from the anode 3.

Emitting Layer

In the first exemplary embodiment, the emitting layer 5 includes a first compound, second compound and third compound. The first compound, second compound and third compound are different compounds.

In the first exemplary embodiment, a singlet energy S(M1) of the first compound and a singlet energy S(M2) of the second compound satisfy a numerical formula (Numerical Formula 1) below. An electron affinity Af(M1) of the first compound and an electron affinity Af(M2) of the second compound satisfy a numerical formula (Numerical Formula 2) below. A triplet energy T(M1) of the first compound satisfies a numerical formula (Numerical Formula 3) below.

$$S(M2) \geq S(M1) \times 0.95 \quad \text{(Numerical Formula 1)}$$

$$Af(M2) - Af(M1) \geq 0.2 \text{ eV} \quad \text{(Numerical Formula 2)}$$

$$T(M1) \leq 2.0 \text{ eV} \quad \text{(Numerical Formula 3)}.$$

According to the organic EL device 1 of the first exemplary embodiment, since electrons injected to the emitting layer 5 are trapped by the second compound when the numerical formula (Numerical Formula 2) is satisfied, deterioration at an interface between the emitting layer 5 and a layer abutting on a side of the emitting layer 5 closer to the anode 3 (i.e., the hole transporting layer 7 in the first exemplary embodiment) is preventable. Moreover, when the numerical formula (Numerical Formula 1) is satisfied, the trapped electrons become more likely to be transferred from the second compound to the first compound, so that probability of recombination of the electrons and holes in the first compound is improved while probability of recombination of the electrons and holes in the second compound is decreased. Accordingly, the organic EL device according to the first exemplary embodiment can emit with a long lifetime.

In the first exemplary embodiment, the singlet energy S(M1) of the first compound and the singlet energy S(M2) of the second compound preferably satisfy a relationship of a numerical formula (Numerical Formula 4) below.

$$S(M2) \geq S(M1) \quad \text{(Numerical Formula 4)}$$

In the first exemplary embodiment, the singlet energy S(M2) of the second compound and a singlet energy S(M3) of the third compound preferably satisfy a relationship of a numerical formula (Numerical Formula 4a) below.

$$S(M2) \geq S(M3) \quad \text{(Numerical Formula 4a)}$$

In the organic EL device 1 of the first exemplary embodiment, when the numerical formula (Numerical Formula 4) is satisfied, the trapped electrons become more likely to be transferred from the second compound to the first compound, so that the probability of recombination of the electrons and holes in the first compound is further improved. As a result, the organic EL device 1 can emit light at more favorable color purity with a longer lifetime.

In the first exemplary embodiment, the singlet energy S(M2) of the second compound preferably satisfy a relationship of a numerical formula (Numerical Formula 5) below, more preferably a relationship of a numerical formula (Numerical Formula 5a).

$$S(M2) \geq 3.0 \text{ eV} \quad \text{(Numerical Formula 5)}$$

$$S(M2) \geq 3.2 \text{ eV} \quad \text{(Numerical Formula 5a)}$$

In the organic EL device 1 of the first exemplary embodiment, when the numerical formula (Numerical Formula 5) and the numerical formula (Numerical Formula 5a) are satisfied, the trapped electrons become more likely to be transferred from the second compound to the first compound, so that the probability of recombination of the electrons and holes in the first compound is further improved. As a result, the organic EL device 1 can emit light at further more favorable color purity with a further longer lifetime.

In the first exemplary embodiment, the electron affinity Af(M1) of the first compound and the electron affinity Af(M2) of the second compound preferably satisfy a relationship of a numerical formula (Numerical Formula 6) below, more preferably a relationship of a numerical formula (Numerical Formula 6a), further preferably a relationship of a numerical formula (Numerical Formula 6b).

$$Af(M2) - Af(M1) > 0.2 \text{ eV} \quad \text{(Numerical Formula 6)}$$

$$Af(M2) - Af(M1) > 0.3 \text{ eV} \quad \text{(Numerical Formula 6a)}$$

$$Af(M2) - Af(M1) > 0.4 \text{ eV} \quad \text{(Numerical Formula 6b)}$$

In the first exemplary embodiment, the electron affinity Af(M2) of the second compound preferably satisfy a relationship of a numerical formula (Numerical Formula 6c)

below, more preferably a relationship of a numerical formula (Numerical Formula 6d).

$$Af(M2)>3.2 \text{ eV} \quad \text{(Numerical Formula 6c)}$$

$$Af(M2)>3.4 \text{ eV} \quad \text{(Numerical Formula 6d)}$$

In the organic EL device 1 of the first exemplary embodiment, when the numerical formulae (Numerical Formula 6) (Numerical Formula 6a) and (Numerical Formula 6b) are satisfied, the electrons injected into the emitting layer 5 become more likely to be trapped by the second compound. Accordingly, deterioration at the interface between the emitting layer 5 and the layer abutting on the side of the emitting layer 5 closer to the anode 3 (i.e., the hole transporting layer 7 in the first exemplary embodiment) is preventable. Moreover, since the electrons become further more likely to be transferred from the second compound to the first compound, the probability of the recombination of the electrons and holes in the first compound is further improved. As a result, the organic EL device 1 can emit light at further more favorable color purity with a further longer lifetime.

In the first exemplary embodiment, the triplet energy T(M1) of the first compound and a triplet energy T(M2) of the second compound preferably satisfy a relationship of a numerical formula (Numerical Formula 7) below.

$$T(M1)<T(M2) \quad \text{(Numerical Formula 7)}$$

In the organic EL device 1 of the first exemplary embodiment, when the numerical formula (Numerical Formula 7) is satisfied, triplet excitons generated by the recombination of the electrons and holes in the first compound are less likely to be transferred to the second compound having the triplet energy higher than the first compound. Moreover, even when the triplet excitons are generated in the second compound, the triplet excitons quickly energy-transfer to the first compound. As a result, TTF (Triplet-Triplet Fusion) phenomenon, in which the triplet excitons collide with one another to generate singlet excitons, efficiently occurs in molecules of the first compound. The TTF phenomenon is disclosed in, for instance, International Publication No. WO2010/134352, International Publication No. WO2010/143434, International Publication No. WO2012/070233, and International Publication No. WO2012/070234.

Singlet Energy S

Singlet energy S is measured as follows.

A 10 μmol/L toluene solution of a measurement target compound is prepared and put in a quartz cell. An absorption spectrum (ordinate axis: luminous intensity, abscissa axis: wavelength) of the thus-obtained sample is measured at a normal temperature (300K). A tangent is drawn to the fall of the absorption spectrum on the long-wavelength side, and a wavelength value λedge (nm) at an intersection of the tangent and the abscissa axis is assigned to a conversion equation 1 below to calculate singlet energy. A unit of the singlet energy S is denoted by eV.

$$S \text{ (eV)}=1239.85/\lambda\text{edge} \quad \text{Conversion equation 1:}$$

In the exemplary embodiment, the absorption spectrum is measured using a spectrophotometer (U3310 manufactured by Hitachi, Ltd.). It should be noted that the absorption spectrum measuring device may be different from the above device.

The tangent to the fall of the absorption spectrum on the long-wavelength side is drawn as follows. While moving on a curve of the absorption spectrum from the maximum spectral value closest to the long-wavelength side in a long-wavelength direction, a tangent at each point on the curve is checked. An inclination of the tangent is decreased and increased in a repeated manner as the curve falls (i.e., a value of the ordinate axis is decreased). A tangent drawn at a point of the minimum inclination closest to the long-wavelength side (except when absorbance is 0.1 or less) is defined as the tangent to the fall of the absorption spectrum on the long-wavelength side.

The maximum absorbance of 0.2 or less is not included in the above-mentioned maximum absorbance on the long-wavelength side.

Ionization Potential Ip

Ionization potential can be measured using a photoelectron spectroscope under atmosphere. Specifically, a material is irradiated with light and the amount of electrons generated by charge separation is measured. The photoelectron spectroscope is exemplified by a photoelectron spectroscope (product name: AC-3) manufactured by RIKEN KEIKI Co., Ltd. A unit of the ionization potential Ip is denoted by eV.

Electron Affinity Af

The electron affinity can be calculated in accordance with a conversion equation (Numerical Formula 9) using the ionization potential Ip and the measurement value of the singlet energy S of the compounds measured by the above method. A unit of the electron affinity is denoted by eV.

$$Af=Ip-S \quad \text{(Numerical Formula 9)}$$

Triplet Energy T

The triplet energy is measured as follows. Firstly, a measurement target compound is deposited on a quartz substrate to prepare a sample. A phosphorescent spectrum (ordinate axis: phosphorescent luminous intensity, abscissa axis: wavelength) of the sample is measured at a low temperature (77K). A tangent is drawn to the rise of the phosphorescent spectrum on the short-wavelength side. The triplet energy is calculated by a conversion equation 2 below based on a wavelength value λedge (nm) at an intersection of the tangent and the abscissa axis. A unit of the triplet energy T is denoted by eV.

$$T \text{ (eV)}=1239.85/\lambda\text{edge} \quad \text{Conversion equation 2:}$$

The tangent to the rise of the phosphorescence spectrum on the short-wavelength side is drawn as follows. While moving on a curve of the phosphorescence spectrum from the short-wavelength side to the maximum spectral value closest to the short-wavelength side among the maximum spectral values, a tangent is checked at each point on the curve toward the long-wavelength of the phosphorescence spectrum. An inclination of the tangent is increased as the curve rises (i.e., a value of the ordinate axis is increased). A tangent drawn at a point of the maximum inclination (i.e., a tangent at an inflection point) is defined as the tangent to the rise of the phosphorescence spectrum on the short-wavelength side.

The maximum with peak intensity being 15% or less of the maximum peak intensity of the spectrum is not included in the above-mentioned maximum closest to the short-wavelength side of the spectrum. The tangent drawn at a point of the maximum spectral value being closest to the short-wavelength side and having the maximum inclination is defined as a tangent to the rise of the phosphorescence spectrum on the short-wavelength side.

For phosphorescence measurement, a spectrophotofluorometer body F-4500 (manufactured by Hitachi High-Technologies Corporation) is usable. The measurement instrument is not limited to this arrangement. A combination of a cooling unit, a low temperature container, an excitation light source and a light-receiving unit may be used for measurement.

First Compound

In the first exemplary embodiment, the first compound is not particularly limited as long as the first compound satisfies the relationships of the numerical formulae (Numerical Formula 1) (Numerical Formula 2) and (Numerical Formula 3).

In this exemplary embodiment, the first compound is also preferably an anthracene derivative.

Moreover, for instance, in the exemplary embodiment, the first compound is also preferably represented by a formula (1) below.

[Formula 1]

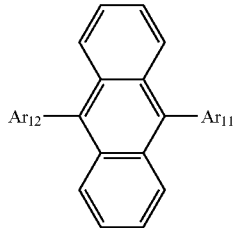

(1)

In the formula (1), $Ar_{11}$ and $Ar_{12}$ are each independently a substituted or unsubstituted aromatic hydrocarbon group having 6 to 30 ring carbon atoms, or substituted or unsubstituted heterocyclic group having 5 to 30 ring atoms.

It is preferable that $Ar_{11}$ and $Ar_{12}$ are each independently a substituted or unsubstituted phenyl group.

It is also preferable that $Ar_{11}$ is a substituted or unsubstituted naphthyl group and $Ar_{12}$ is a substituted or unsubstituted phenyl group.

$Ar_{11}$ is also preferably any one group selected from the group consisting of a substituted or unsubstituted phenanthryl group, substituted or unsubstituted benzoanthryl group, 9,9-dimethylfluorenyl group, 9,9-diphenylfluorenyl group, substituted or unsubstituted dibenzofuranyl group, substituted or unsubstituted dibenzothiophenyl group, substituted or unsubstituted naphthobenzofuranyl group, substituted or unsubstituted naphthobenzothiophenyl group, and substituted or unsubstituted naphthobenzofluorenyl group. $Ar_{12}$ is also preferably one of a substituted or unsubstituted phenyl group and a substituted or unsubstituted naphthyl group.

For instance, in the exemplary embodiment, the first compound is also preferably represented by a formula (10) below.

[Formula 2]

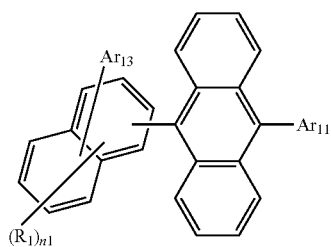

(10)

In the formula (10), $Ar_{13}$ is a substituted or unsubstituted aromatic hydrocarbon group having 6 to 30 ring carbon atoms, or a substituted or unsubstituted heterocyclic group having 5 to 30 ring atoms.

$Ar_{13}$ is bonded to any carbon atom in a naphthalene ring.

$Ar_{11}$ is a substituted or unsubstituted aromatic hydrocarbon group having 6 to 30 ring carbon atoms.

n1 is 6. A plurality of $R_1$ may be mutually the same or different.

$R_1$ is each independently a hydrogen atom or a substituent. When $R_1$ is a substituent, the substituent is selected from the group consisting of a halogen atom, a hydroxyl group, a cyano group, a substituted or unsubstituted alkyl group having 1 to 30 carbon atoms, a substituted or unsubstituted alkoxy group having 1 to 30 carbon atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a silyl group represented by $-Si(R_{100})_3$, an amino group represented by $-N(R_{101})_2$, a substituted or unsubstituted aromatic hydrocarbon group having 6 to 30 ring carbon atoms, and a substituted or unsubstituted heterocyclic group having 5 to 30 ring atoms.

$R_{100}$ is each independently a hydrogen atom or a substituent. When $R_{100}$ is a substituent, the substituent is a substituted or unsubstituted alkyl group having 1 to 30 carbon atoms or a substituted or unsubstituted aromatic hydrocarbon group having 6 to 30 ring carbon atoms.

A plurality of $R_{100}$ are mutually the same or different.

$R_{101}$ is each independently a hydrogen atom or a substituent. When $R_{101}$ is a substituent, the substituent is a substituted or unsubstituted alkyl group having 1 to 30 carbon atoms or a substituted or unsubstituted aromatic hydrocarbon group having 6 to 30 ring carbon atoms.

A plurality of $R_{101}$ are mutually the same or different.

It should be noted that an anthracene ring bonded with $Ar_{13}$ is bonded to any carbon atom in a naphthalene ring.

For instance, in the exemplary embodiment, the first compound is also preferably represented by a formula (10a) below.

[Formula 3]

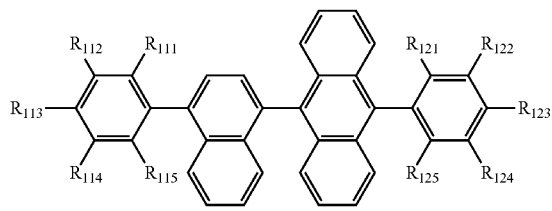

(10a)

In the formula (10a), $R_{111}$ to $R_{115}$ and $R_{121}$ to $R_{125}$ are each independently a hydrogen atom or a substituent. When $R_{111}$ to $R_{115}$ and $R_{121}$ to $R_{125}$ are substituents, each of the substituents is selected from the examples of the substituents listed when $R_1$ is a substituent.

When at least two of $R_{111}$ to $R_{115}$ are substituents bonded to carbon atoms of a six-membered ring, the substituents to two carbon atoms may be bonded to each other to form a ring.

When at least two of $R_{121}$ to $R_{125}$ are substituents bonded to carbon atoms of a six-membered ring, the substituents to two carbon atoms may be bonded to each other to form a ring. Moreover, in the exemplary embodiment, $R_{111}$ to $R_{115}$ and $R_{121}$ to $R_{125}$ are also preferably hydrogen atoms.

For instance, in the exemplary embodiment, the first compound is also preferably represented by a formula (11) below.

[Formula 4]

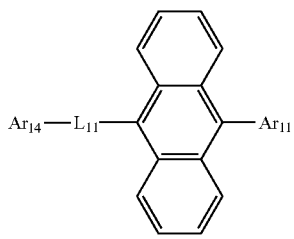

(11)

In the formula (11): $Ar_{11}$ is a substituted or unsubstituted aromatic hydrocarbon group having 6 to 30 ring carbon atoms or a substituted or unsubstituted heterocyclic group having 5 to 30 ring atoms.

$L_{11}$ is a single bond or a linking group.

The linking group in $L_{11}$ is each independently a substituted or unsubstituted aromatic hydrocarbon group having 6 to 30 ring carbon atoms or a substituted or unsubstituted heterocyclic group having 5 to 30 ring atoms.

$Ar_{14}$ is a group represented by a formula (11a) below or a group represented by a formula (11b) below.

[Formula 5]

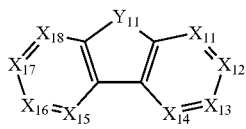

(11a)

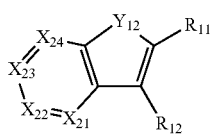

(11b)

In the formula (11a): $Y_{11}$ is an oxygen atom, a sulfur atom, or $C(R_{102})_2$; and $R_{102}$ is each independently a hydrogen atom or a substituent. When $R_{102}$ is a substituent, the substituent is a substituted or unsubstituted alkyl group having 1 to 30 carbon atoms or a substituted or unsubstituted aromatic hydrocarbon group having 6 to 30 ring carbon atoms.

$X_{11}$ to $X_{18}$ are each independently a carbon atom bonded to Rx, a carbon atom bonded to $L_{11}$, a carbon atom bonded to a structure represented by a formula (11c) below, or a carbon atom bonded to a structure represented by a formula (11d) below.

$R_x$ is each independently a hydrogen atom or a substituent. When $R_x$ is a substituent, the substituent is selected from the examples of the substituents listed when $R_1$ is a substituent. A plurality of $R_x$ may be mutually the same or different.

In the formula (11b): $Y_{12}$ is an oxygen atom, a sulfur atom, or $C(R_{103})_2$; and $R_{103}$ is each independently a hydrogen atom or a substituent. When $R_{103}$ is a substituent, the substituent is a substituted or unsubstituted alkyl group having 1 to 30 carbon atoms or a substituted or unsubstituted aromatic hydrocarbon group having 6 to 30 ring carbon atoms.

$X_{21}$ to $X_{24}$ are each independently a carbon atom bonded to $R_y$, a carbon atom bonded to $L_{11}$, or a carbon atom bonded to a structure represented by a formula (11d) below.

$R_{11}$, $R_{12}$, and $R_y$ are each independently a hydrogen atom or a substituent. When $R_y$ is a substituent, the substituent is selected from the examples of the substituents listed when $R_1$ is a substituent. A plurality of $R_y$ may be mutually the same or different.

[Formula 6]

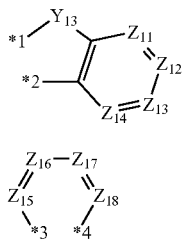

(11c)

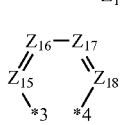

(11d)

In the formula (11c), *1 and *2 each independently represent a bonding position to a carbon atom in a set selected from a set of $X_{11}$ and $X_{12}$, a set of $X_{12}$ and $X_{13}$, a set of $X_{13}$ and $X_{14}$, a set of $X_{15}$ and $X_{16}$, a set of $X_{16}$ and $X_{17}$, and a set of $X_{17}$ and $X_{18}$.

$Y_{13}$ is an oxygen atom, a sulfur atom, or $C(R_{104})_2$.

$R_{104}$ is each independently a hydrogen atom or a substituent. When $R_{104}$ is a substituent, the substituent is a substituted or unsubstituted alkyl group having 1 to 30 carbon atoms or a substituted or unsubstituted aromatic hydrocarbon group having 6 to 30 ring carbon atoms.

$Z_{11}$ to $Z_{14}$ are each independently a carbon atom bonded to $R_Z$, or a carbon atom bonded to $L_{11}$.

$R_Z$ is each independently a hydrogen atom or a substituent. When $R_Z$ is a substituent, the substituent is selected from the examples of the substituents listed when $R_1$ is a substituent. A plurality of $R_Z$ may be mutually the same or different.

In the formula (11d), *3 and *4 each independently represent a bonding position to a carbon atom in a set selected from a set of $X_{11}$ and $X_{12}$, a set of $X_{12}$ and $X_{13}$, a set of $X_{13}$ and $X_{14}$, a set of $X_{15}$ and $X_{16}$, a set of $X_{16}$ and $X_{17}$, and a set of $X_{17}$ and $X_{18}$, or a bonding position to a carbon atom in a set selected from a set of $X_{21}$ and $X_{22}$, a set of $X_{22}$ and $X_{23}$, and a set of $X_{23}$ and $X_{24}$.

$Z_{15}$ to $Z_{18}$ are each independently a carbon atom bonded to $R_W$, or a carbon atom bonded to $L_{11}$.

$R_W$ is each independently a hydrogen atom or a substituent. When $R_W$ is a substituent, the substituent is selected from the examples of the substituents listed when $R_1$ is a substituent. A plurality of $R_W$ may be mutually the same or different.

When the structure represented by the formula (11c) is bonded to the group represented by the formula (11a), any one of $X_{11}$ to $X_{18}$ and $Z_{11}$ to $Z_{14}$ is a carbon atom bonded to $L_{11}$.

When the structure represented by the formula (11d) is bonded to the group represented by the formula (11a), any one of $X_{11}$ to $X_{18}$ and $Z_{15}$ to $Z_{18}$ is a carbon atom bonded to $L_{11}$.

When the structure represented by the formula (11d) is bonded to the group represented by the formula (11b), any one of $X_{21}$ to $X_{24}$ and $Z_{15}$ to $Z_{18}$ is a carbon atom bonded to $L_{11}$.

$Ar_{14}$ is also preferably a group represented by a formula (11e), (11f), (11g) or (11h) below.

[Formula 7]

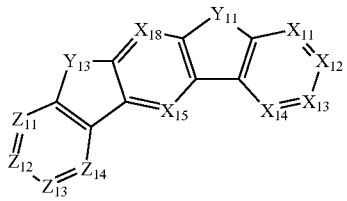

(11e)

[Formula 8]

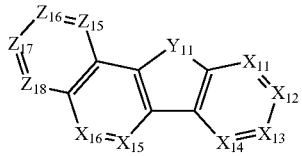

(11f)

[Formula 9]

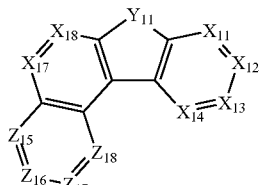

(11g)

[Formula 10]

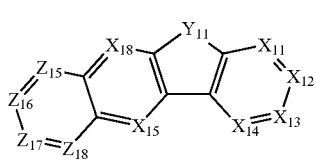

(11h)

In the formulae formula (11e), (11f), (11g) and (11h), $Y_{11}$ represents the same as $Y_{11}$ in the formula (11a).

$Y_{13}$ represents the same as $Y_{13}$ in the formula (11c).

$X_{11}$ to $X_{18}$ are each independently a carbon atom bonded to Rx, or a carbon atom bonded to $L_{11}$.

$R_x$ is each independently a hydrogen atom or a substituent. When $R_x$ is a substituent, the substituent is selected from the examples of the substituents listed when $R_1$ is a substituent. A plurality of $R_x$ may be mutually the same or different.

$Z_{11}$ to $Z_{14}$ are each independently a carbon atom bonded to $R_Z$, or a carbon atom bonded to $L_{11}$.

$R_Z$ is each independently a hydrogen atom or a substituent. When $R_Z$ is a substituent, the substituent is selected from the examples of the substituents listed when $R_1$ is a substituent. A plurality of $R_Z$ may be mutually the same or different.

$Z_{15}$ to $Z_{18}$ are each independently a carbon atom bonded to $R_W$, or a carbon atom bonded to $L_{11}$.

$R_W$ is each independently a hydrogen atom or a substituent. When $R_W$ is a substituent, the substituent is selected from the examples of the substituents listed when $R_1$ is a substituent. A plurality of $R_W$ may be mutually the same or different.

In the formula (11e), any one of $X_{11}$ to $X_{15}$, $X_{18}$, and $Z_{11}$ to $Z_{14}$ is a carbon atom bonded to $L_{11}$.

In the formula (11f), any one of $X_{11}$ to $X_{16}$ and $Z_{15}$ to $Z_{18}$ is a carbon atom bonded to $L_{11}$.

In the formula (11g), any one of $X_{11}$ to $X_{14}$, $X_{17}$, $X_{18}$, and $Z_{15}$ to $Z_{18}$ is a carbon atom bonded to $L_{11}$.

In the formula (11h), any one of $X_{11}$ to $X_{15}$, $X_{18}$, and $Z_{15}$ to $Z_{18}$ is a carbon atom bonded to $L_{11}$.

$Y_{11}$ is preferably an oxygen atom. When $Y_{11}$ is an oxygen atom, $X_{13}$ is preferably a carbon atom to be bonded to $L_{11}$.

For instance, in the exemplary embodiment, the first compound is also preferably represented by a formula (12) below.

[Formula 11]

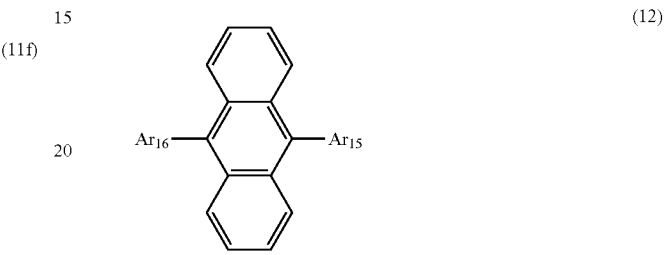

(12)

In the formula (12), $Ar_{15}$ and $Ar_{16}$ are each independently a substituted or unsubstituted aromatic hydrocarbon group having 6 to 30 ring carbon atoms, or a substituted or unsubstituted heterocyclic group having 5 to 30 ring atoms. However, at least one of $Ar_{15}$ and $Ar_{16}$ is a substituted or unsubstituted fused aromatic hydrocarbon group in which two or three six-membered rings are fused.

In the formula (12), when $Ar_{15}$ is an unsubstituted phenyl group and $Ar_{16}$ is a group represented by a formula (12a) below, in other words, when the first compound represented by a formula (12b) below, $R_{131}$ is preferably a substituted or unsubstituted aromatic hydrocarbon group having 10 to 30 ring carbon atoms or a substituted or unsubstituted heterocyclic group having 5 to 30 ring atoms.

[Formula 12]

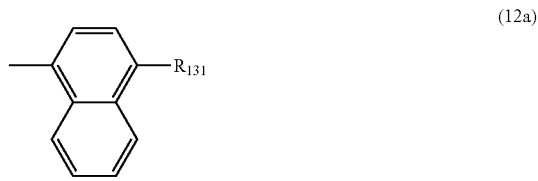

(12a)

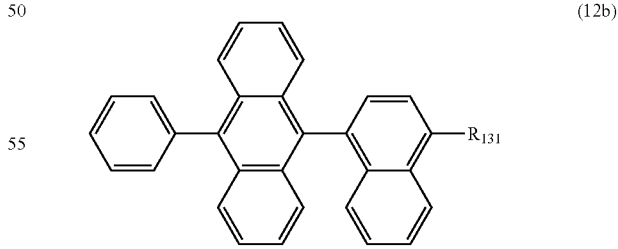

(12b)

In the formula (12), $Ar_{15}$ is an unsubstituted phenyl group and $Ar_{16}$ is a group represented by a formula (12c) below, in other words, when the first compound represented by a formula (12d) below, $R_{132}$ is preferably an unsubstituted aromatic hydrocarbon group having 6 to 14 ring carbon atoms or a substituted or unsubstituted heterocyclic group having 5 to 30 ring atoms.

[Formula 13]

(12c)

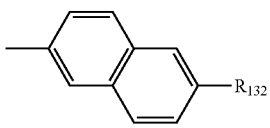

(12d)

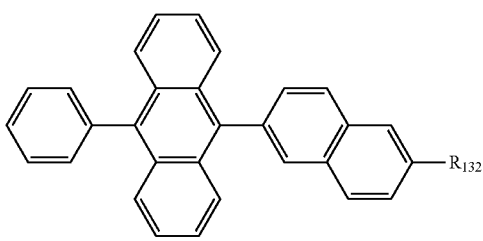

In the formula (12), $Ar_{15}$ is an unsubstituted phenyl group and $Ar_{16}$ is a group represented by a formula (12e) below, in other words, when the first compound represented by a formula (12f) below, $R_{133}$ is preferably an unsubstituted aromatic hydrocarbon group having 12 to 30 ring carbon atoms or a substituted or unsubstituted heterocyclic group having 5 to 30 ring atoms.

[Formula 14]

(12e)

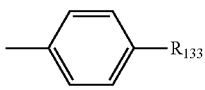

(12f)

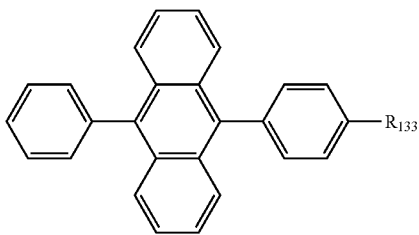

In the formula (12): it is preferable that $Ar_{15}$ is an unsubstituted 1-naphthyl group; $Ar_{16}$ is a group represented by a formula (12g) below, a group represented by a formula (12i) below, a substituted or unsubstituted aromatic hydrocarbon group having 12 to 30 ring carbon atoms or a substituted or unsubstituted heterocyclic group having 5 to 30 ring atoms.

When $Ar_{15}$ is an unsubstituted 1-naphthyl group and $Ar_{16}$ is the group represented by the formula (12g) below, the first compound is represented by a formula (12h) below.

When $Ar_{15}$ is an unsubstituted 1-naphthyl group and $Ar_{16}$ is the group represented by the formula (12i) below, the first compound is represented by a formula (12j) below.

[Formula 15]

(12g)

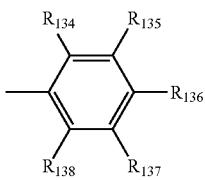

(12h)

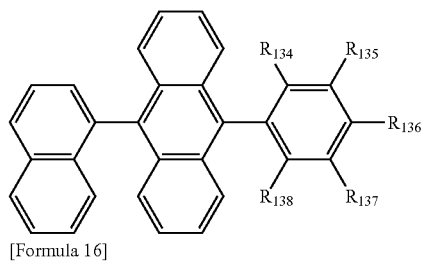

[Formula 16]

(12i)

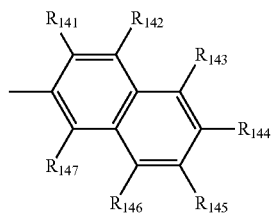

(12j)

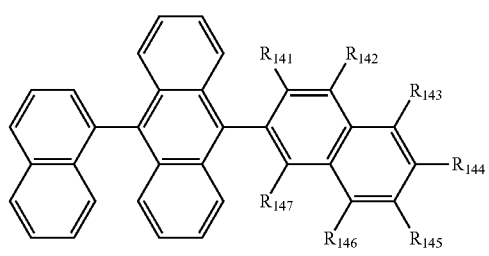

In the formulae (12g) and (12h), $R_{134}$ to $R_{138}$ are each independently a hydrogen atom or a substituent. When $R_{134}$ to $R_{138}$ are substituents, each of the substituents is selected from the examples of the substituents listed when $R_1$ is a substituent, and at least one of $R_{134}$ to $R_{138}$ is a substituted or unsubstituted aromatic hydrocarbon group having 6 to 30 ring carbon atoms or a substituted or unsubstituted heterocyclic group having 5 to 30 ring atoms.

In the formulae (12i) and (12j), $R_{141}$ to $R_{147}$ are each independently a hydrogen atom or a substituent. When $R_{141}$ to $R_{147}$ are substituents, each of the substituents is selected from the examples of the substituents listed when $R_1$ is a substituent, and at least one of $R_{141}$ to $R_{147}$ is a substituted or unsubstituted aromatic hydrocarbon group having 6 to 30 ring carbon atoms or a substituted or unsubstituted heterocyclic group having 5 to 30 ring atoms.

For instance, in the exemplary embodiment, the first compound is also preferably represented by a formula (12k) below.

[Formula 17]

(12k)

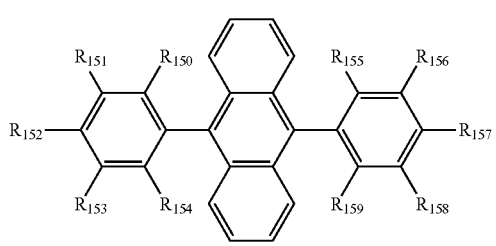

In the formula (12k), $R_{150}$ to $R_{159}$ are each independently a hydrogen atom or a substituent. When $R_{150}$ to $R_{159}$ are substituents, each of the substituents is selected from the examples of the substituents listed when $R_1$ is a substituent.

At least one of $R_{150}$ to $R_{159}$ is a substituted or unsubstituted alkyl group having 1 to 10 carbon atoms, a substituted or unsubstituted cycloalkyl group having 3 to 10 ring carbon atoms, a substituted or unsubstituted aromatic hydrocarbon group having 6 to 30 ring carbon atoms, or a substituted or unsubstituted heterocyclic group having 5 to 30 ring atoms.

When at least two of $R_{150}$ to $R_{154}$ are substituents bonded to carbon atoms of a six-membered ring, the substituents may be bonded to each other to form a ring.

For instance, in the exemplary embodiment, the first compound is also preferably represented by a formula (12m) below.

[Formula 18]

(12m)

[Chemical structure showing anthracene with two substituted phenyl/naphthyl groups, positions labeled $R_{160}$ through $R_{166}$ and $R_{171}$ through $R_{175}$]

In the formula (12m), $R_{160}$ to $R_{166}$ and $R_{171}$ to $R_{175}$ are each independently a hydrogen atom or a substituent. When $R_{160}$ to $R_{166}$ and $R_{171}$ to $R_{175}$ are substituents, each of the substituents is selected from the examples of the substituents listed when $R_1$ is a substituent. When one of $R_{160}$ to $R_{166}$ is a substituted or unsubstituted aromatic hydrocarbon group, the aromatic hydrocarbon group has 10 to 30 ring carbon atoms. At least one of $R_{171}$ to $R_{175}$ is also preferably a substituted or unsubstituted fused aromatic hydrocarbon group having 10 to 30 ring carbon atoms, more preferably a substituted or unsubstituted fused aromatic hydrocarbon group having 10 to 14 ring carbon atoms. When at least one of $R_{171}$ to $R_{175}$ is a substituted or unsubstituted fused aromatic hydrocarbon group having 10 to 30 ring carbon atoms, it is preferable that the rest of $R_{171}$ to $R_{175}$ are hydrogen atoms and $R_{160}$ to $R_{166}$ are also hydrogen atoms.

For instance, in the exemplary embodiment, the first compound is also preferably represented by a formula (13) below.

[Formula 19]

(13)

$$Ar_{17}-L_{17}-\text{[anthracene]}-L_{18}-Ar_{18}$$

In the formula (13), $Ar_{17}$ and $Ar_{18}$ are each independently a substituted or unsubstituted aromatic hydrocarbon group having 6 to 30 ring carbon atoms, or a substituted or unsubstituted heterocyclic group having 5 to 30 ring atoms.

However, one of $Ar_{17}$ and $Ar_{18}$ is a substituted or unsubstituted fused aromatic hydrocarbon group having 16 to 30 ring carbon atoms.

$L_{17}$ and $L_{18}$ are each independently a single bond or a linking group. The linking group in $L_{17}$ and $L_{18}$ is a substituted or unsubstituted aromatic hydrocarbon group having 6 to 18 ring carbon atoms, or a substituted or unsubstituted heterocyclic group having 5 to 30 ring carbon atoms.

For instance, in the exemplary embodiment, the first compound is also preferably represented by a formula (13a) below.

[Formula 20]

(13a)

[Chemical structure with anthracene connected via $L_{17}$ to $Ar_{17}$ and via $L_{18}$ to a fused aromatic ring system with positions $R_{181}$ through $R_{191}$]

In the formula (13a), $Ar_{17}$ is a substituted or unsubstituted aromatic hydrocarbon group having 6 to 30 ring carbon atoms, or a substituted or unsubstituted heterocyclic group having 5 to 30 ring atoms.

$L_{17}$ and $L_{18}$ each independently represent the same as $L_{17}$ and $L_{18}$ of the formula (13).

$R_{181}$ to $R_{191}$ are each independently a hydrogen atom or a substituent. When $R_{181}$ to $R_{191}$ are substituents, each of the substituents is selected from the examples of the substituents listed when $R_1$ is a substituent.

When at least two of $R_{181}$ to $R_{191}$ are substituents, the substituents may be bonded to each other to form a ring.

In the exemplary embodiment, $R_{181}$ to $R_{191}$ are also preferably hydrogen atoms.

For instance, in the exemplary embodiment, the first compound is also preferably represented by a formula (13b) below.

[Formula 21]

(13b)

[Chemical structure with anthracene connected to $Ar_{17}$ (with $n2$ $R_{192}$ substituents) and via $L_{18}$ to a fused aromatic ring system with positions $Rx_1$ through $Rx_{11}$]

In the formula (13b), $Ar_{17}$ is a substituted or unsubstituted aromatic hydrocarbon group having 6 to 30 ring carbon atoms, or a substituted or unsubstituted heterocyclic group having 5 to 30 ring atoms.

$L_{18}$ represents the same as $L_{18}$ in the formula (13).

n2 is 4. A plurality of $R_{192}$ may be mutually the same or different.

$R_{192}$ and $Rx_1$ to $Rx_{11}$ are each independently a hydrogen atom or a substituent. When $R_{192}$ and $Rx_1$ to $Rx_{11}$ are substituents, each of the substituents is selected from the examples of the substituents listed when $R_1$ is a substituent.

When at least two of $Rx_1$ to $Rx_{11}$ are substituents, the substituents may be bonded to each other to form a ring.

In the exemplary embodiment, it is also preferable that $Ar_{11}$ to $Ar_{18}$ are each independently a substituted or unsubstituted aromatic hydrocarbon group having 6 to 30 ring carbon atoms.

Moreover, in the exemplary embodiment, $Ar_{11}$ to $Ar_{18}$ are also preferably an aromatic hydrocarbon group selected from the group consisting of a substituted or unsubstituted phenyl group, substituted or unsubstituted biphenyl group, substituted or unsubstituted biphenyl group, substituted or unsubstituted terphenyl group, substituted or unsubstituted naphthyl group, substituted or unsubstituted anthryl group, substituted or unsubstituted phenanthryl group, and substituted or unsubstituted triphenylenyl group.

For instance, in the exemplary embodiment, the first compound is also preferably represented by a formula (13c) below.

[Formula 22]

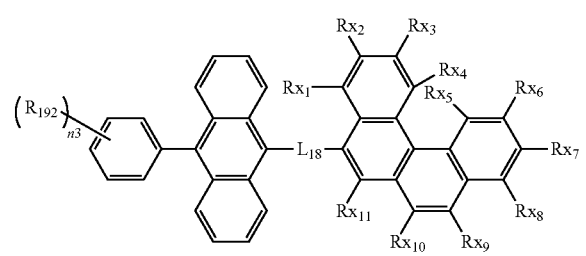

(13c)

In the formula (13c), $L_{18}$ represents the same as $L_{18}$ in the formula (13).

n3 is 5. A plurality of $R_{192}$ may be mutually the same or different.

$R_{192}$ and $Rx_1$ to $Rx_{11}$ are each independently a hydrogen atom or a substituent. When $R_{192}$ and $Rx_1$ to $Rx_{11}$ are substituents, each of the substituents is selected from the examples of the substituents listed when $R_1$ is a substituent.

When at least two of $Rx_1$ to $Rx_{11}$ are substituents, the substituents may be bonded to each other to form a ring.

In the exemplary embodiment, $R_{192}$ and $Rx_1$ to $Rx_{11}$ are also preferably hydrogen atoms.

In the exemplary embodiment, $R_1$, $R_{11}$, $R_{12}$, $R_{131}$ to $R_{138}$, $R_{141}$ to $R_{147}$, $R_{150}$ to $R_{166}$, $R_{171}$ to $R_{175}$, $R_{181}$ to $R_{192}$, and $Rx_1$ to $Rx_{11}$ are each independently a hydrogen atom or a substituent. When $R_1$, $R_{11}$, $R_{12}$, $R_{131}$ to $R_{138}$, $R_{141}$ to $R_{147}$, $R_{150}$ to $R_{166}$, $R_{171}$ to $R_{175}$, $R_{181}$ to $R_{192}$, and $Rx_1$ to $Rx_{11}$ are substituents, each of the substituents is preferably a substituent selected from the group consisting of a halogen atom, substituted or unsubstituted alkyl group having 1 to 30 carbon atoms, substituted or unsubstituted alkoxy having 1 to 30 carbon atoms, silyl represented by $-Si(R_{105})_3$, and substituted or unsubstituted aromatic hydrocarbon group having 6 to 30 ring carbon atoms. $R_{105}$ is each independently a hydrogen atom or a substituent. When $R_{105}$ is a substituent, the substituent is a substituted or unsubstituted alkyl group having 1 to 30 carbon atoms, or a substituted or unsubstituted aromatic hydrocarbon group having 6 to 30 ring carbon atoms.

Second Compound

In the exemplary embodiment, the second compound is not particularly limited as long as the second compound satisfies the relationships of the numerical formulae (Numerical Formula 1) and (Numerical Formula 2).

For instance, in the exemplary embodiment, the second compound is preferably represented by a formula (21) below.

[Formula 23]

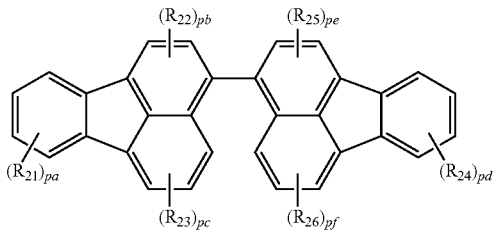

(21)

In the formula (21), $R_{21}$ to $R_{26}$ are each independently a hydrogen atom or a substituent. When $R_{21}$ to $R_{26}$ are substituents, each of the substituents is a substituent selected from the group consisting of a halogen atom, a hydroxyl group, a cyano group, a substituted or unsubstituted alkyl group having 1 to 30 carbon atoms, a substituted or unsubstituted alkoxy group having 1 to 30 carbon atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a silyl group represented by $-Si(R_{221})_3$, an amino group represented by $-N(R_{222})_2$, a substituted or unsubstituted aromatic hydrocarbon group having 6 to 30 ring carbon atoms, and a substituted or unsubstituted heterocyclic group having 5 to 30 ring atoms.

$R_{221}$ is each independently a hydrogen atom or a substituent. When $R_{221}$ is a substituent, the substituent is a substituted or unsubstituted alkyl group having 1 to 30 carbon atoms, or a substituted or unsubstituted aromatic hydrocarbon group having 6 to 30 ring carbon atoms.

A plurality of $R_{221}$ are mutually the same or different.

$R_{222}$ is each independently a hydrogen atom or a substituent. When $R_{222}$ is a substituent, the substituent is a substituted or unsubstituted alkyl group having 1 to 30 carbon atoms, or a substituted or unsubstituted aromatic hydrocarbon group having 6 to 30 ring carbon atoms.

A plurality of $R_{222}$ are mutually the same or different.

pa is 4. A plurality of $R_{21}$ may be mutually the same or different.

pb is 2. A plurality of $R_{22}$ may be mutually the same or different.

pc is 3. A plurality of $R_{23}$ may be mutually the same or different.

pd is 4. A plurality of $R_{24}$ may be mutually the same or different.

pe is 2. A plurality of $R_{25}$ may be mutually the same or different.

pf is 3. A plurality of $R_{26}$ may be mutually the same or different.

Each of $R_{21}$ to $R_{26}$ is bonded to a carbon atom of each of the aromatic rings.

In the exemplary embodiment, when $R_{21}$ to $R_{26}$ are substituents, each of the substituents is preferably selected from the group consisting of a substituted or unsubstituted alkyl group having 1 to 30 carbon atoms, a silyl group represented by —Si(R$_{223}$)$_3$, a substituted or unsubstituted aromatic hydrocarbon group having 6 to 30 ring carbon atoms, and substituted or unsubstituted heterocyclic group having 5 to 30 ring atoms. R$_{223}$ each independently represents the same as R$_{221}$.

Moreover, in the exemplary embodiment, R$_{21}$ to R$_{26}$ are also preferably hydrogen atoms. In this case, the second compound is represented by a formula (21a) below.

[Formula 24]

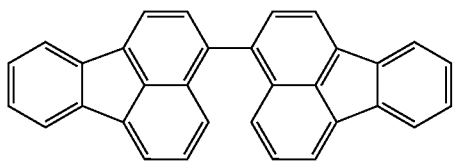

(21a)

Moreover, in the exemplary embodiment, the second compound is also preferably a compound having a cyano group.

For instance, in the exemplary embodiment, the second compound is also preferably represented by a formula (22) below.

[Formula 25]

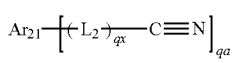

(22)

In the formula (22), Ar$_{21}$ is a substituted or unsubstituted fused aromatic hydrocarbon group having 10 to 30 ring carbon atoms.

L$_2$ is a single bond or a linking group.

The linking group in L$_2$ is a substituted or unsubstituted aromatic hydrocarbon group having 6 to 30 ring carbon atoms, or a substituted or unsubstituted heterocyclic group having 5 to 30 ring atoms.

qx is an integer from 1 to 3. A plurality of L$_2$ may be mutually the same or different.

qa is an integer from 1 to 4. A plurality of group represented by a formula (22x) below bonded to Ar$_{21}$ may be mutually the same or different.

[Formula 26]

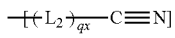

(22x)

The formula (22) in which qx is 1 is represented by a formula (22a) below. The formula (22) in which qx is 2 is represented by a formula (22b) below. The formula (22) in which qx is 3 is represented by a formula (22c) below.

[Formula 27]

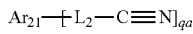

(22a)

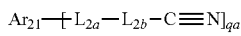

(22b)

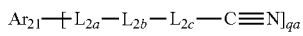

(22c)

In the formulae (22a), (22b) and (22c), Ar$_{21}$ and qa respectively represent the same as Ar$_{21}$ and qa in the formula (22).

In the formulae (22a), (22b) and (22c), L$_2$, L$_2$a, L$_2$b and L$_2$c each represent the same as L$_2$ in the formula (22).

In the exemplary embodiment, qa is preferably an integer from 1 to 3, more preferably 1 or 2.

In the exemplary embodiment, the substituted or unsubstituted fused aromatic hydrocarbon group having 10 to 30 ring carbon atoms in Ar$_{21}$ is preferably a group derived from a fused aromatic hydrocarbon selected from the group consisting of naphthalene, anthracene, phenanthrene, fluorene, pyrene, chrysene, fluoranthene, benzo[a]anthracene, benzo[c]phenanthrene, triphenylene, benzo[g]chrysene, benzo[b]triphenylene, picene, and perylene.

The substituted or unsubstituted fused aromatic hydrocarbon group having 10 to 30 ring carbon atoms in Ar$_{21}$ is more preferably a group derived from a fused aromatic hydrocarbon selected from the group consisting of phenanthrene, pyrene, chrysene, fluoranthene, triphenylene, and benzo[g]chrysene.

When Ar$_{21}$ has a substituent, the substituent is selected from the examples of the substituents listed when R$_{21}$ to R$_{26}$ are the substituents, preferably a substituted or unsubstituted alkyl group having 1 to 30 carbon atoms, a silyl group represented by —Si(R$_{224}$)$_3$, a substituted or unsubstituted aromatic hydrocarbon group having 6 to 30 ring carbon atoms, and substituted or unsubstituted heterocyclic group having 5 to 30 ring atoms. R$_{224}$ each independently represents the same as R$_{221}$.

For instance, in the exemplary embodiment, the second compound is also preferably represented by a formula (23) below.

[Formula 28]

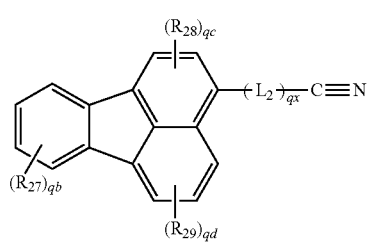

(23)

In the formula (23), L$_2$ represents the same as L$_2$ in the formula (22).

R$_{27}$ to R$_{29}$ are each independently a hydrogen atom or a substituent. When R$_{27}$ to R$_{29}$ are substituents, each of the substituents is selected from the examples of the substituents listed when R$_{21}$ to R$_{26}$ are the substituents.

qb is 4. A plurality of R$_{27}$ may be mutually the same or different.

qc is 2. A plurality of R$_{28}$ may be mutually the same or different.

qd is 3. A plurality of R$_{29}$ may be mutually the same or different.

qx is an integer from 1 to 3. A plurality of L$_2$ may be mutually the same or different.

Each of R$_{27}$ to R$_{29}$ is bonded to a carbon atom of each of the aromatic rings.

In the exemplary embodiment, it is preferable that L$_2$ is a linking group and the linking group in L$_2$ is a substituted or unsubstituted aromatic hydrocarbon group having 6 to 30 ring carbon atoms. It is also preferable that qx is 2 or 3 and the plurality of L$_2$ are each independently a substituted or unsubstituted aromatic hydrocarbon group having 6 to 30 ring carbon atoms. Moreover, $L_2$ is preferably a phenylene group, biphenyldiyl group, or naphthylene group. The linking group in $L_2$ preferably includes a phenylene group bonded with a cyano group at a meta position or a para position.

For instance, in the exemplary embodiment, the second compound is also preferably represented by a formula (23x) below.

[Formula 29]

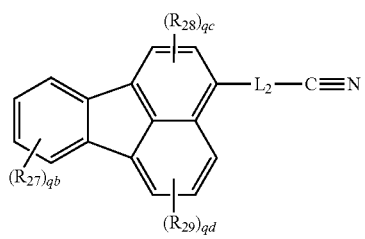

(23x)

In the formula (23x), $L_2$ represents the same as $L_2$ in the formula (22).

$R_{27}$ to $R_{29}$ are each independently a hydrogen atom or a substituent. When $R_{27}$ to $R_{29}$ are substituents, each of the substituents is selected from the examples of the substituents listed when $R_{21}$ to $R_{26}$ are the substituents.

qb is 4. A plurality of $R_{27}$ may be mutually the same or different.

qc is 2. A plurality of $R_{28}$ may be mutually the same or different.

qd is 3. A plurality of $R_{29}$ may be mutually the same or different.

Each of $R_{27}$ to $R_{29}$ is bonded to a carbon atom of each of the aromatic rings.

Moreover, for instance, the second compound is also preferably represented by a formula (23a) below.

[Formula 30]

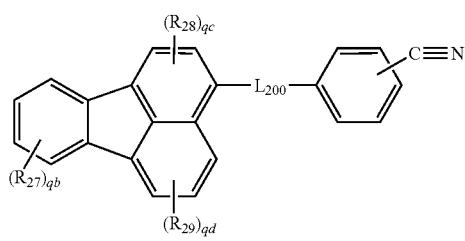

(23a)

In the formula (23a), $R_{27}$ to $R_{29}$ each are a hydrogen atom or a substituent. When $R_{27}$ to $R_{29}$ are substituents, each of the substituents is selected from the examples of the substituents listed when $R_{21}$ to $R_{26}$ are the substituents.

$L_{200}$ each independently represent a single bond or a linking group. When $L_{200}$ is a linking group, $L_{200}$ represents the same as $L_2$. A cyano group is bonded to a carbon atom of a six-membered ring of a phenyl group, preferably at a para position or a meta position. Each of $R_{27}$ to $R_{29}$ is bonded to a carbon atom of each of the aromatic rings.

In the exemplary embodiment, when $R_{27}$ to $R_{29}$ are substituents, each of the substituents is preferably selected from the group consisting of a substituted or unsubstituted alkyl group having 1 to 30 carbon atoms, a silyl group represented by —Si($R_{225}$)$_3$, a substituted or unsubstituted aromatic hydrocarbon group having 6 to 30 ring carbon atoms, and substituted or unsubstituted heterocyclic group having 5 to 30 ring atoms. $R_{225}$ each independently represents the same as $R_{221}$.

In the exemplary embodiment, $R_{27}$ to $R_{29}$ are also preferably hydrogen atoms.

For instance, in the exemplary embodiment, the second compound is also preferably represented by a formula (24) below.

[Formula 31]

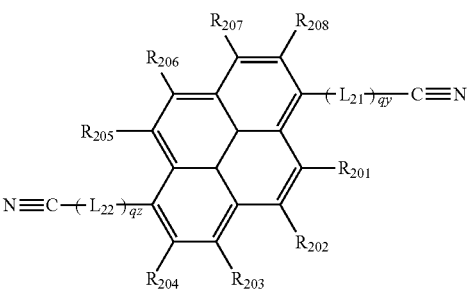

(24)

In the formula (24), $R_{201}$ to $R_{208}$ are each independently a hydrogen atom or a substituent. When $R_{201}$ to $R_{208}$ are substituents, each of the substituents is selected from the examples of the substituents listed when $R_{21}$ to $R_{26}$ are the substituents.

$L_{21}$ and $L_{22}$ each independently represent the same as $L_2$ of the formula (22).

qy is an integer from 1 to 3. A plurality of $L_{21}$ may be mutually the same or different.

qz is an integer from 1 to 3. A plurality of $L_{22}$ may be mutually the same or different.

In the exemplary embodiment, it is preferable that $L_{21}$ and $L_{22}$ are linking groups and each of the linking groups in $L_{21}$ and $L_{22}$ is a substituted or unsubstituted aromatic hydrocarbon group having 6 to 30 ring carbon atoms. It is also preferable that qy and qz are each independently 2 or 3 and the plurality of $L_{21}$ and $L_{22}$ are each independently selected from the group consisting a substituted or unsubstituted aromatic hydrocarbon group having 6 to 30 ring carbon atoms. Moreover, it is preferable that $L_{21}$ and $L_{22}$ are each independently a phenylene group, biphenyldiyl group, or naphthylene group. The linking group in $L_{21}$ and $L_{22}$ preferably includes a phenylene group bonded with a cyano group at a meta position or a para position.

For instance, in the exemplary embodiment, the second compound is also preferably represented by a formula (24a) below.

[Formula 32]

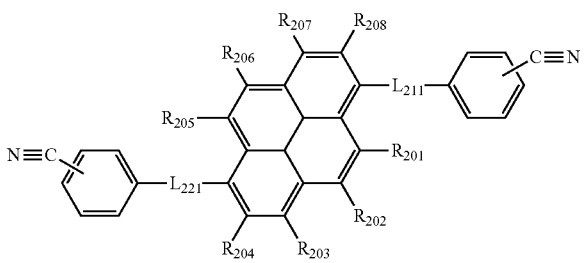

(24a)

In the formula (24a), $R_{201}$ to $R_{208}$ each independently represent the same as $R_{201}$ to $R_{208}$ of the formula (24).

$L_{211}$ and $L_{221}$ are each independently a single bond or a linking group. When $L_{211}$ and $L_{221}$ are linking groups, $L_{211}$ and $L_{221}$ each represent the same as $L_{21}$ and $L_{22}$. A cyano group is bonded to a carbon atom of a six-membered ring of a phenyl group, preferably at a para position or a meta position.

In the exemplary embodiment, when $R_{201}$ to $R_{208}$ are substituents, each of the substituents is preferably selected from the group consisting of a substituted or unsubstituted alkyl group having 1 to 30 carbon atoms, a silyl group represented by $-Si(R_{226})_3$, a substituted or unsubstituted aromatic hydrocarbon group having 6 to 30 ring carbon atoms, and substituted or unsubstituted heterocyclic group having 5 to 30 ring atoms. $R_{226}$ each independently represents the same as $R_{221}$.

In the exemplary embodiment, $R_{201}$ to $R_{208}$ are also preferably hydrogen atoms.

For instance, in the exemplary embodiment, the second compound is also preferably represented by a formula (25) below.

[Formula 33]

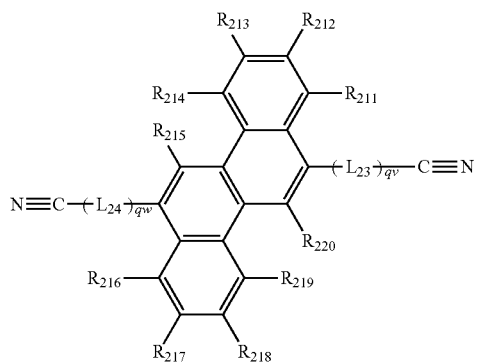

(25)

In the formula (25), $R_{211}$ to $R_{220}$ are each independently a hydrogen atom or a substituent. When $R_{211}$ to $R_{220}$ are substituents, each of the substituents is selected from the examples of the substituents listed when $R_{21}$ to $R_{26}$ are the substituents.

$L_{23}$ and $L_{24}$ each independently represent the same as $L_2$ of the formula (22).

qv is an integer from 1 to 3. A plurality of $L_{23}$ may be mutually the same or different.

qw is an integer from 1 to 3. A plurality of $L_{24}$ may be mutually the same or different.

In the exemplary embodiment, it is preferable that $L_{23}$ and $L_{24}$ are linking groups and each of the linking groups in $L_{23}$ and $L_{24}$ is a substituted or unsubstituted aromatic hydrocarbon group having 6 to 30 ring carbon atoms. It is also preferable that qv and qw are each independently 2 or 3 and the plurality of $L_{23}$ and $L_{24}$ are each independently selected from the group consisting of a substituted or unsubstituted aromatic hydrocarbon group having 6 to 30 ring carbon atoms. Moreover, it is preferable that $L_{23}$ and $L_{24}$ are each independently a phenylene group, biphenyldiyl group, or naphthylene group. The linking group in $L_{23}$ and $L_{24}$ preferably includes a phenylene group bonded with a cyano group at a meta position or a para position.

For instance, the second compound is also preferably represented by a formula (25a) below.

[Formula 34]

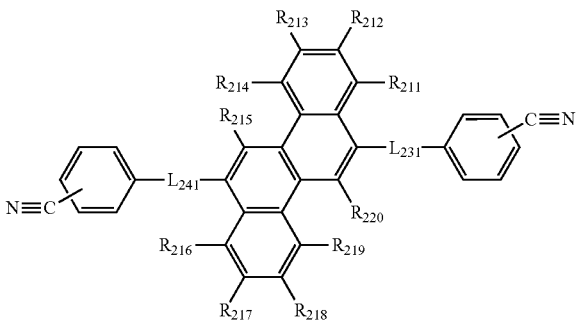

(25a)

In the formula (25a), $R_{211}$ to $R_{220}$ each independently represent the same as $R_{211}$ to $R_{220}$ of the formula (25).

$L_{231}$ and $L_{241}$ are each independently a single bond or a linking group. When $L_{231}$ and $L_{241}$ are linking groups, $L_{231}$ and $L_{241}$ each represent the same as $L_{23}$ and $L_{24}$. A cyano group is bonded to a carbon atom of a six-membered ring of a phenyl group, preferably at a para position or a meta position.

In the exemplary embodiment, when $R_{211}$ to $R_{220}$ are substituents, each of the substituents is preferably selected from the group consisting of a substituted or unsubstituted alkyl group having 1 to 30 carbon atoms, a silyl group represented by $-Si(R_{227})_3$, a substituted or unsubstituted aromatic hydrocarbon group having 6 to 30 ring carbon atoms, and substituted or unsubstituted heterocyclic group having 5 to 30 ring atoms. $R_{227}$ each independently represents the same as $R_{221}$.

In the exemplary embodiment, $R_{211}$ to $R_{220}$ are also preferably hydrogen atoms.

Third Compound

The third compound in the exemplary embodiment is not particularly limited.

In the organic EL device 1 according to the exemplary embodiment, an ionization potential Ip(M3) of the third compound and an ionization potential Ip(M1) of the first compound preferably satisfy a relationship of a numerical formula (Numerical Formula 10) below, more preferably a relationship of a numerical formula (Numerical Formula 10a), further preferably a relationship of a numerical formula (Numerical Formula 10b).

$Ip(M1)-Ip(M3) \geq 0.2$ eV   (Numerical Formula 10)

$Ip(M1)-Ip(M3) > 0.2$ eV   (Numerical Formula 10a)

$Ip(M1)-Ip(M3) > 0.3$ eV   (Numerical Formula 10b)

In the organic EL device 1 according to the exemplary embodiment, since holes injected to the emitting layer 5 are easily trapped by the third compound when the numerical formula (Numerical Formula 10), (Numerical Formula 10a) or (Numerical Formula 10b) is satisfied, deterioration at an interface between the emitting layer 5 and a layer abutting on a side of the emitting layer 5 closer to the cathode 4 (i.e., the electron transporting layer 8 in the exemplary embodiment) is prevented.

The third compound in the exemplary embodiment is preferably a fluorescent material.

Moreover, in the exemplary embodiment, a triplet energy T(M3) of the third compound and the triplet energy T(M1) of the first compound preferably satisfy a relationship of a numerical formula (Numerical Formula 11) below.

$$T(M1) < T(M3) \quad \text{(Numerical Formula 11)}$$

In the organic EL device 1 of the first exemplary embodiment, when the numerical formula (Numerical Formula 11) is satisfied, triplet excitons generated by the recombination of the electrons and holes in the first compound are less likely to be transferred to the third compound having the triplet energy higher than the first compound. Moreover, even when the triplet excitons are generated in the third compound, the triplet excitons quickly energy-transfer to the first compound. As a result, TTF phenomenon, in which the triplet excitons collide with one another to generate singlet excitons, efficiently occurs in molecules of the first compound.

Moreover, in the exemplary embodiment, the singlet energy S(M3) of the third compound and the singlet energy S(M1) of the first compound preferably satisfy a relationship of a numerical formula (Numerical Formula 12) below.

$$S(M1) > S(M3) \quad \text{(Numerical Formula 12)}$$

In the organic EL device 1 of the exemplary embodiment, when the numerical formula (Numerical Formula 12) is satisfied, singlet excitons generated by the recombination of the electrons and holes in molecules of the first compound and singlet excitons generated by the TTF phenomenon are easily transferred to the third compound, which contributes to fluorescence of the third compound. As a result, a luminous efficiency of the organic EL device 1 is further improved. Moreover, since the third compound mainly emits while emission of the first compound and the second compound coexisting in the emitting layer 5 is inhibited, the organic EL device 1 emits in an emission color of the third compound, in other words, in a single color. Moreover, a half bandwidth of a main peak of luminescence spectrum of the organic EL device 1 is narrow and a color purity becomes further favorable.

The third compound in the exemplary embodiment is more preferably a compound satisfying the relationships of the numerical formulae (Numerical Formula 11 and Numerical Formula 12).

As the third compound in the exemplary embodiment, a fluorescent material is usable. Examples of the fluorescent material include a bisarylamino naphthalene derivative, an aryl-substituted naphthalene derivative, a bisarylamino anthracene derivative, an aryl-substituted anthracene derivative, a bisarylamino pyrene derivative, an aryl-substituted pyrene derivative, a bisarylamino chrysene derivative, an aryl-substituted chrysene derivative, a bisarylamino fluoranthene derivative, an aryl-substituted fluoranthene derivative, an indenoperylene derivative, a pyrromethene boron complex compound, a compound having a pyrromethene skeleton or a metal complex thereof, a diketopyrrolopyrrole derivative, and a perylene derivative.

Examples of a blue fluorescent material usable in the emitting layer 5 include a pyrene derivative, styrylamine derivative, chrysene derivative, fluoranthene derivative, fluorene derivative, diamine derivative, and triarylamine derivative. Specific examples of the blue fluorescent material include N,N'-bis[4-(9H-carbazole-9-yl)phenyl]-N,N'-diphenylstilbene-4,4'-diamine (abbreviation: YGA2S), 4-(9H-carbazole-9-yl)-4'-(10-phenyl-9-anthryl)triphenylamine (abbreviation: YGAPA), and 4-(10-phenyl-9-anthryl)-4'-(9-phenyl-9H-carbazole-3-yl)triphenylamine (abbreviation: PCBAPA).

A green fluorescent material usable in the emitting layer 5 is exemplified by an aromatic amine derivative. Specific examples of the green fluorescent material include N-(9,10-diphenyl-2-anthryl)-N,9-diphenyl-9H-carbazole-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazole-9-yl)phenyl]-N-phenylanthracene-2-amine (abbreviation: 2YGABPhA), and N,N,9-triphenylanthracene-9-amine (abbreviation: DPhAPhA).

Examples of a red fluorescent material usable in the emitting layer 5 include a tetracene derivative and a diamine derivative. Specific examples of the red fluorescent material include N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-a]fluoranthene-3,10-diamine (abbreviation: p-mPhAFD).

In the exemplary embodiment, the third compound preferably exhibits fluorescence having a main peak wavelength of 550 nm or less, more preferably of 480 nm or less. The main peak wavelength means a peak wavelength of luminescence spectrum exhibiting a maximum luminous intensity among luminous spectra measured in a toluene solution in which the third compound is dissolved at a concentration from $10^{-6}$ mol/L to $10^{-5}$ mol/L.

The third compound preferably exhibits a blue fluorescence. Moreover, the third compound is preferably a material having a high fluorescence quantum efficiency.

For instance, in the exemplary embodiment, the third compound is also preferably represented by a formula (30) below.

[Formula 35]

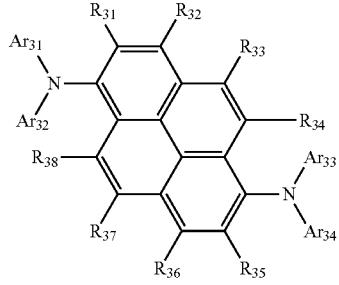

(30)

In the formula (30), $R_{31}$ to $R_{38}$ are each independently a hydrogen atom or a substituent. When $R_{31}$ to $R_{38}$ are substituents, each of the substituents is a substituent selected from the group consisting of a halogen atom, a hydroxyl group, a cyano group, a substituted or unsubstituted alkyl group having 1 to 30 carbon atoms, a substituted or unsubstituted alkoxy group having 1 to 30 carbon atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a silyl group represented by —Si($R_{300}$)$_3$, an amino group represented by —N(R$_{301}$)$_2$, a substituted or unsubstituted aromatic hydrocarbon group having 6 to 30 ring carbon atoms, and a substituted or unsubstituted heterocyclic group having 5 to 30 ring atoms.

R$_{300}$ is each independently a hydrogen atom or a substituent. When R$_{300}$ is a substituent, the substituent is a substituted or unsubstituted alkyl group having 1 to 30 carbon atoms, or a substituted or unsubstituted aromatic hydrocarbon group having 6 to 30 ring carbon atoms.

A plurality of R$_{300}$ are mutually the same or different.

R$_{301}$ is each independently a hydrogen atom or a substituent. When R$_{301}$ is a substituent, the substituent is a substituted or unsubstituted alkyl group having 1 to 30 carbon atoms, or a substituted or unsubstituted aromatic hydrocarbon group having 6 to 30 ring carbon atoms.

A plurality of R$_{301}$ are mutually the same or different.

Ar$_{31}$ to Ar$_{34}$ are each independently a substituted or unsubstituted aromatic hydrocarbon group having 6 to 30 ring carbon atoms, or a heterocyclic group represented by a formula (30a) below.

[Formula 36]

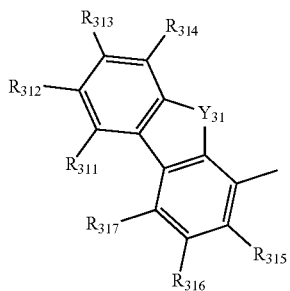

(30a)

In the formula (30a), R$_{311}$ to R$_{317}$ are each independently a hydrogen atom or a substituent. When R$_{311}$ to R$_{317}$ are substituents, each of the substituents is selected from the examples of the substituents listed when R$_{31}$ to R$_{38}$ are the substituents.

When at least two of R$_{311}$ to R$_{317}$ are substituents, the substituents may be bonded to each other to form a ring.

Y$_{31}$ is an oxygen atom or a sulfur atom.

When R$_{31}$ to R$_{38}$ and R$_{311}$ to R$_{317}$ are substituents, each of the substituents is preferably selected from the group consisting of a halogen atom, a cyano group, a substituted or unsubstituted alkyl group having 1 to 30 carbon atoms, a silyl group represented by —Si(R$_{302}$)$_3$, and a substituted or unsubstituted aromatic hydrocarbon group having 6 to 30 ring carbon atoms. R$_{302}$ represents the same as R$_{300}$.

In the emitting layer 5, it is preferable to employ a doping system in which the first compound is used as a host material, the second compound is used as a co-host material, and the third compound is used as a dopant material. When the doping system is employed, the host material has a function to mainly promote recombination of electrons and holes and trap excitons within the emitting layer while the dopant material has a function to promote an efficient emission from the excitons obtained by the recombination. In the exemplary embodiment, the co-host material has a function to trap and transfer carriers to the host material in order to increase generation of excitons in the host material.

Film Thickness of Emitting Layer

A film thickness of the emitting layer 5 of the organic EL device 1 in the exemplary embodiment is preferably in a range of 5 nm to 50 nm, more preferably in a range of 7 nm to 50 nm, further preferably in a range of 10 nm to 50 nm. The film thickness of less than 5 nm may cause difficulty in forming the emitting layer and in controlling chromaticity, while the film thickness of more than 50 nm may raise drive voltage.

Content Ratio of Compounds in Emitting Layer

In the emitting layer 5 of the organic EL device 1 of the exemplary embodiment, a content ratio of the first compound is preferably in a range from 50 mass % to 95 mass %, a content ratio of the second compound is preferably in a range from 1 mass % to 50 mass %, a content ratio of the third compound is preferably in a range from 1 mass % to 10 mass %. An upper limit of a total content ratio of the first compound, second compound and third compound in the emitting layer 5 is 100 mass %. It should be noted that the first exemplary embodiment does not exclude an arrangement in which a material other than the first compound, second compound and third compound is contained in the emitting layer 5.

Substrate

The substrate 2 is used as a support for the organic EL device 1. Examples of the substrate 2 include a glass substrate, quartz substrate, and plastic substrate. Moreover, a flexible substrate may be used. The flexible substrate means a bendable substrate. Examples of the flexible substrate include plastic substrates formed of polycarbonate, polyarylate, polyethersulfone, polypropylene, polyester, polyvinyl fluoride, polyvinyl chloride, polyimide, and polyethylene naphthalate. Moreover, an inorganic deposited film is also usable as the substrate.

Anode

Preferable examples of a material for the anode 3 formed on the substrate 2 include metal, an alloy, an electroconductive compound, and a mixture thereof, which have a large work function (specifically, 4.0 eV or more). Specific examples of the material include indium oxide-tin oxide (ITO: Indium Tin Oxide), indium oxide-tin oxide containing silicon or silicon oxide, indium oxide-zinc oxide, and indium oxide containing tungsten oxide and zinc oxide, and graphene. In addition, the examples of the material further include gold (Au), platinum (Pt), nickel (Ni), tungsten (W), chrome (Cr), molybdenum (Mo), iron (Fe), cobalt (Co), copper (Cu), palladium (Pd), titanium (Ti), and a nitride of a metal material (e.g., titanium nitride).

The material is typically formed into a film by a sputtering method. For instance, the indium oxide-zinc oxide can be formed by the sputtering method using a target in which zinc oxide in a range from 1 mass % to 10 mass % is added to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, the anode 3 may be formed by a vacuum deposition method, a coating method, an inkjet method, a spin coating method or the like.

Among the organic layers formed on the anode 3, since the hole injecting layer 6 abutting on the anode 3 is formed of a composite material into which holes are easily injectable irrespective of the work function of the anode 3, a material usable as an electrode material (e.g., metal, an alloy, an electroconductive compound, a mixture thereof, and the elements belonging to the group 1 or 2 of the periodic table) is also usable for the anode 3.

The elements belonging to the group 1 or 2 of the periodic table, which are a material having a small work function, specifically, an alkali metal such as lithium (Li) and cesium (Cs), an alkaline earth metal such as magnesium (Mg), calcium (Ca) and strontium (Sr), an alloy containing the alkali metal and the alkaline earth metal (e.g., MgAg, AlLi), a rare earth metal such as europium (Eu) and ytterbium (Yb), and an alloy containing the rare earth metal are usable for the anode 3. It should be noted that the vacuum deposition method and the sputtering method are usable for forming the anode 3 using the alkali metal, alkaline earth metal and the alloy thereof. Further, when a silver paste is used for the anode 3, the coating method and the inkjet method are usable.

Hole Injecting Layer

The hole injecting layer 6 is a layer containing a substance exhibiting a high hole injectability. Examples of the substance exhibiting a high hole injectability include molybdenum oxide, titanium oxide, vanadium oxide, rhenium oxide, ruthenium oxide, chrome oxide, zirconium oxide, hafnium oxide, tantalum oxide, silver oxide, tungsten oxide, and manganese oxide.

Moreover, examples of the substance exhibiting a high hole injectability further include: an aromatic amine compound, which is a low molecular organic compound, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis [N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl) amino]-9-phenylcarbazole (abbreviation: PCzPCN1); and dipyrazino[2,3-f:20,30-h]quinoxaline-2,3,6,7,10,11-hexacarbonitrile (HAT-CN).

In addition, a high polymer compound (e.g., oligomer, dendrimer and polymer) is usable as the substance exhibiting a high hole injectability. Examples of the high polymer compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl) benzidine] (abbreviation: Poly-TPD). Moreover, an acid-added high polymer compound such as poly(3,4-ethylenedioxythiophene)/poly(styrene sulfonic acid) (PEDOT/PSS) and polyaniline/poly (styrene sulfonic acid) (PAni/PSS) are also usable.

Hole Transporting Layer

The hole transporting layer 7 is a layer containing a substance exhibiting a high hole transportability. An aromatic amine compound, carbazole derivative, anthracene derivative and the like are usable for the hole transporting layer 7. Specific examples of the substance usable for the hole transporting layer 7 include an aromatic amine compound such as 4,4'-bis[N-(1-naphthyl)-N-phenylamino]biphenyl (abbreviation: NPB) ⁀ N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The substance described herein is a substance mainly having a hole mobility of $10^{-6}$ cm$^2$/Vs or more.

For the hole transporting layer 7, a carbazole derivative such as CBP, 9-[4-(N-carbazolyl)]phenyl-10-phenylanthracene (CzPA), and 9-phenyl-3-[4-(10-phenyl-9-anthryl)phenyl]-9H-carbazole (PCzPA) and an anthracene derivative such as t-BuDNA, DNA, and DPAnth may be used. A high polymer compound such as poly(N-vinylcarbazole) (abbreviation: PVK) and poly(4-vinyltriphenylamine) (abbreviation: PVTPA) is also usable.

However, in addition to the above substances, any substance exhibiting a higher hole transportability than an electron transportability may be used. It should be noted that the layer containing the substance exhibiting a high hole transportability may be not only a single layer but also a laminate of two or more layers formed of the above substance.

When two or more hole transporting layers are provided, one of the hole transporting layers containing a material having a larger energy gap is preferably provided closer to the emitting layer 5.

In the exemplary embodiment, the hole transporting layer 7 preferably has a function to prevent triplet excitons generated in the emitting layer 5 from diffusing to the hole transporting layer 7 and trap the triplet excitons in the emitting layer 5. Trapping the triplet excitons in the emitting layer 5 improves a density of the triplet excitons to efficiently cause the TTF phenomenon. In order to prevent diffusion of the triplet excitons, a triplet energy T(Ht) of the hole transporting layer 7 is preferably larger than T(M1). By satisfying such a relationship of the triplet energy, the hole transporting layer 7 prevents diffusion of the triplet excitons.

Electron Transporting Layer

The electron transporting layer 8 is a layer containing a substance exhibiting a high electron transportability. For the electron transporting layer 8, 1) a metal complex such as an aluminum complex, beryllium complex, and zinc complex, 2) a hetero aromatic compound such as imidazole derivative, benzimidazole derivative, azine derivative, carbazole derivative, and phenanthroline derivative, and 3) a high polymer compound are usable. Specifically, as a low molecular organic compound, the metal complex such as Alq, tris(4-methyl-8-quinolinolato)aluminum (abbreviation: Almq3), bis(10-hydroxybenzo[h]quinolinato)beryllium (abbreviation: BeBq2), BAlq, Znq, ZnPBO, and ZnBTZ are usable. In addition to the metal complex, the hetero aromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzooxazole-2-yl)stilbene (abbreviation: BzOs) are usable. In the exemplary embodiment, a benzoimidazole compound is preferably usable. The substance described herein is a substance mainly having an electron mobility of $10^{-6}$ cm$^2$/Vs or more. It should be noted that any substance other than the above substance may be used for the electron transporting layer 8 as long as the substance exhibits a higher electron transportability than the hole transportability. Moreover, the electron transporting layer 8 may be not only a single layer but also a laminate of two or more layers formed of the above substance(s).

Moreover, a high polymer compound is usable for the electron transporting layer 8. Examples of the high polymer compound include poly[(9,9-dihexylfluorene-2,7-diyl)-co-(pyridine-3,5-diyl)] (abbreviation: PF-Py) and poly[(9,9-dioctylfluorene-2,7-diyl)-co-(2,2'-bipyridine-6,6'-diyl)] (abbreviation: PF-BPy).

In the exemplary embodiment, the electron transporting layer 8 preferably has a function to prevent triplet excitons generated in the emitting layer 5 from diffusing to the electron transporting layer 8 and the electron injecting layer 9 and trap the triplet excitons in the emitting layer 5. Trapping the triplet excitons in the emitting layer 5 improves a density of the triplet excitons to efficiently cause the TTF phenomenon. In order to prevent diffusion of the triplet excitons, a triplet energy T(Et) of the electron transporting layer 8 is preferably larger than T(M1), more preferably larger than T(M3). By satisfying such a relationship of the triplet energy, the electron transporting layer 8 prevents diffusion of the triplet excitons.

Electron Injecting Layer

The electron injecting layer 9 is a layer containing a substance exhibiting a high electron injectability. For the electron injecting layer 9, an alkali metal, alkaline earth metal or a compound thereof are usable, examples of which include lithium (Li), cesium (Cs), calcium (Ca), lithium fluoride (LiF), cesium fluoride (CsF), calcium fluoride (CaF2), and lithium oxide (LiOx). In addition, the alkali metal, alkaline earth metal or the compound thereof may be added to the substance exhibiting the electron transportability in use. Specifically, for instance, magnesium (Mg) added to Alq may be used. In this case, the electrons can be more efficiently injected form the anode 4.

Alternatively, the electron injecting layer 9 may be provided by a composite material in a form of a mixture of the organic compound and the electron donor. Such a composite material exhibits excellent electron injectability and electron transportability since electrons are generated in the organic compound by the electron donor. In this case, the organic compound is preferably a material excellent in transporting the generated electrons. Specifically, the above examples (e.g., the metal complex and the hetero aromatic compound) of the substance forming the electron transporting layer 8 are usable. As the electron donor, any substance exhibiting electron donating performance to the organic compound is usable. Specifically, the electron donor is preferably alkali metal, alkaline earth metal and rare earth metal such as lithium, cesium, magnesium, calcium, erbium and ytterbium. The electron donor is also preferably alkali metal oxide and alkaline earth metal oxide such as lithium oxide, calcium oxide, and barium oxide. Moreover, a Lewis base such as magnesium oxide is usable. Further, the organic compound such as tetrathiafulvalene (abbreviation: TTF) is usable.

Cathode

It is preferable to use metal, an alloy, an electroconductive compound, and a mixture thereof, which have a small work function (specifically, 3.8 eV or less) for the cathode 4. Examples of such a material for the cathode include the elements belonging to the group 1 or 2 of the periodic table, specifically, an alkali metal such as lithium (Li) and cesium (Cs), an alkaline earth metal such as magnesium (Mg), calcium (Ca) and strontium (Sr), an alloy containing the alkali metal and the alkaline earth metal (e.g., MgAg, AlLi), a rare earth metal such as europium (Eu) and ytterbium (Yb), and an alloy containing the rare earth metal.

It should be noted that the vacuum deposition method and the sputtering method are usable for forming the cathode 4 using the alkali metal, alkaline earth metal and the alloy thereof. Further, when a silver paste is used for the cathode 4, the coating method and the inkjet method are usable.

By providing the electron injecting layer 9, various conductive materials such as Al, Ag, ITO, graphene, and indium oxide-tin oxide containing silicon or silicon oxide may be used for forming the cathode 4 regardless of the work function. The conductive materials can be formed into a film using the sputtering method, inkjet method, spin coating method and the like.

Layer Formation Method(s)

A method for forming each layer of the organic EL device in the exemplary embodiment is not limited except for the above particular description. However, known methods of dry film-forming such as vacuum deposition, sputtering, plasma or ion plating and wet film-forming such as spin coating, dipping, flow coating or ink-jet are applicable.

Film Thickness

The film thickness of each organic layer of the organic EL device 1 in the exemplary embodiment is subject to no limitation except for the thickness particularly described above. However, the thickness is typically preferably in a range of several nanometers to 1 µm because an excessively thin film is likely to entail defects such as a pin hole while an excessively thick film requires high applied voltage and deteriorates efficiency.

Herein, the ring carbon atoms refer to the number of carbon atoms among atoms forming a ring of a compound (e.g., a monocyclic compound, fused-ring compound, cross-linking compound, carbon ring compound, and heterocyclic compound) in which the atoms are bonded to each other to form the ring. When the ring is substituted by a substituent(s), carbon atom(s) contained in the substituent(s) is not counted in the ring carbon atoms. The same applies to "the ring carbon atoms" described below unless otherwise specified. For instance, a benzene ring has six ring carbon atoms, a naphthalene ring has ten ring carbon atoms, a pyridinyl group has five ring carbon atoms, and a furanyl group has four ring carbon atoms. When a benzene ring and/or a naphthalene ring is substituted by a substituent (e.g., an alkyl group), the number of carbon atoms of the alkyl group is not counted in the number of the ring carbon atoms. When a fluorene ring is substituted by a substituent (e.g., a fluorene ring) (i.e., a spirofluorene ring is included), the number of carbon atoms of the fluorene ring as the substituent is not counted in the number of the ring carbon atoms of the fluorene ring. Herein, the ring atoms refer to the number of atoms forming a ring of a compound (e.g., a monocyclic compound, fused-ring compound, crosslinking compound, carbon ring compound, and heterocyclic compound) in which the atoms are bonded to each other to form the ring (e.g., monocyclic ring, fused ring, ring assembly). An atom(s) not forming the ring (e.g., a hydrogen atom terminating a bond(s) of atoms forming the ring) and an atom(s) of a substituent used for substituting the ring are not counted in the ring atoms. The same applies to "the ring atoms" described below unless otherwise specified. For instance, a pyridine ring has six ring atoms, a quinazoline ring has ten ring atoms, and a furan ring has five ring atoms. A hydrogen atom(s) and/or an atom(s) of a substituent which are bonded to carbon atoms of a pyridine ring and/or quinazoline ring are not counted in the ring atoms. When a fluorene ring is substituted by a substituent (e.g., a fluorene ring) (i.e., a spirofluorene ring is included), the number of atoms of the fluorene ring as the substituent is not counted in the number of the ring atoms of the fluorene ring.

Next, each of the substituents represented by the above formulae will be described below.

Examples of the aromatic hydrocarbon group (occasionally referred to as an aryl group) having 6 to 30 ring carbon atoms in the exemplary embodiment are a phenyl group, biphenyl group, terphenyl group, naphthyl group, anthryl group, phenanthryl group, fluorenyl group, pyrenyl group, chrysenyl group, fluoranthenyl group, benz[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

The aryl group in the exemplary embodiment preferably has 6 to 20 ring carbon atoms, and more preferably has 6 to 12 ring carbon atoms. Among the aryl group, a phenyl group, biphenyl group, naphthyl group, phenanthryl group, terphenyl group and fluorenyl group are particularly preferable. In a 1-fluorenyl group, 2-fluorenyl group, 3-fluorenyl group and 4-fluorenyl group, a carbon atom at a position 9 is preferably substituted by the substituted or unsubstituted alkyl group having 1 to 30 carbon atoms or an unsubstituted aryl group having 6 to 18 ring carbon atoms in a later-described exemplary embodiment.

The heterocyclic group (occasionally referred to as a hetero aryl group, hetero aromatic cyclic group, aromatic heterocyclic group) having 5 to 30 ring atoms in the exemplary embodiment preferably contains, as a hetero atom, at least one atom selected from the group consisting of nitrogen atom, sulfur atom, oxygen atom, silicon atom, selenium atom and germanium atom, more preferably at least one atom selected from the group consisting of nitrogen atom, sulfur atom and oxygen atom.

Examples of the heterocyclic group (occasionally referred to as a hetero aryl group, hetero aromatic cyclic group, aromatic heterocyclic group) having 5 to 30 ring atoms in the exemplary embodiment are a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group.

The heterocyclic group in the exemplary embodiment preferably has 5 to 20 ring atoms, more preferably 5 to 14 ring atoms. Among the above, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are particularly preferable. In 1-carbazolyl group, 2-carbazolyl group, 3-carbazolyl group and 4-carbazolyl group, a nitrogen atom at the ninth position is preferably substituted by a substituted or unsubstituted aryl group having 6 to 30 ring carbon atoms or a substituted or unsubstituted heterocyclic group having 5 to 30 ring atoms according to the exemplary embodiment.

In the exemplary embodiment, the heterocyclic group may be a group derived from partial structures represented by formulae (XY-1) to (XY-18) below.

[Formula 37]

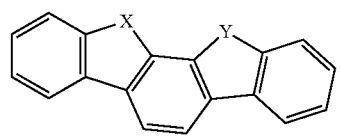
(XY-1)

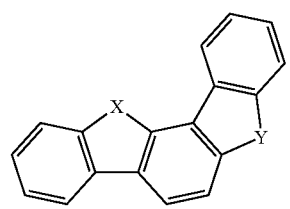
(XY-2)

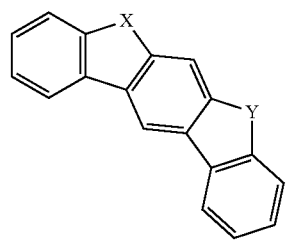
(XY-3)

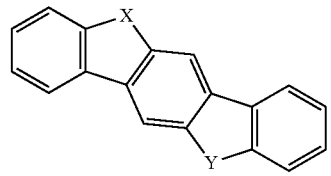
(XY-4)

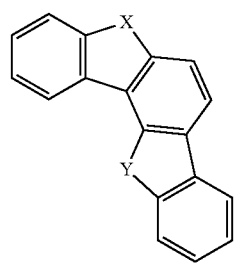
(XY-5)

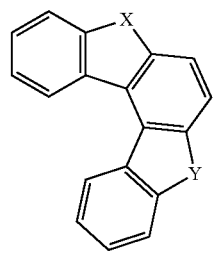
(XY-6)

[Formula 38]

(XY-7) 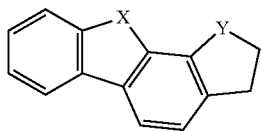

(XY-8) 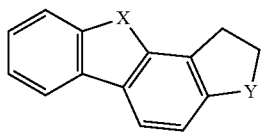

(XY-9) 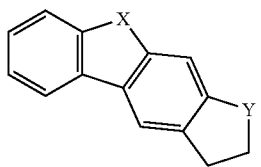

(XY-10) 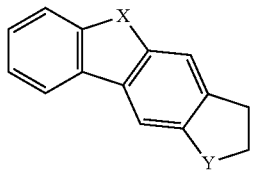

(XY-11) 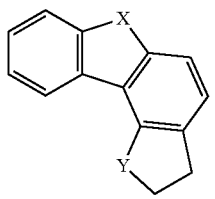

(XY-12) 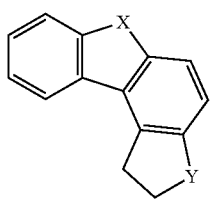

[Formula 39]

(XY-13) 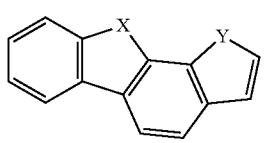

(XY-14) 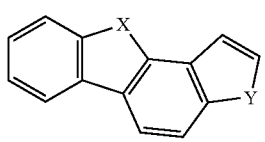

(XY-15) 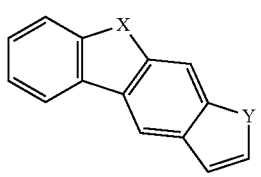

(XY-16) 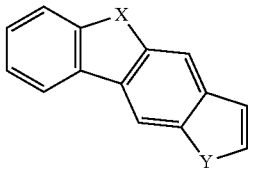

(XY-17) 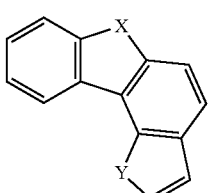

(XY-18) 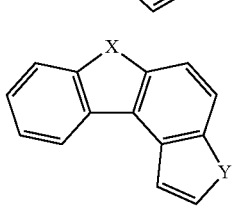

In the formulae (XY-1) to (XY-18), X and Y are each independently a hetero atom, preferably an oxygen atom, sulfur atom, selenium atom, silicon atom, or germanium atom. Each of the partial structures represented by the respective formulae (XY-1) to (XY-18) has a bond at any position to provide a heterocyclic group. The heterocyclic group may be substituted.

In the exemplary embodiment, for instance, a substituted or unsubstituted carbazolyl group may include a group in which a ring is further fused to a carbazole ring represented by a formula below. Such a group may have a substituent. Moreover, the position of the bond may be changed as needed

[Formula 40]

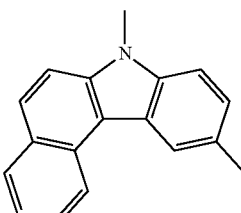 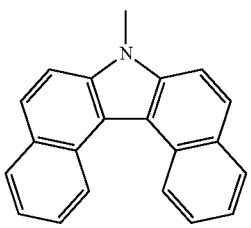

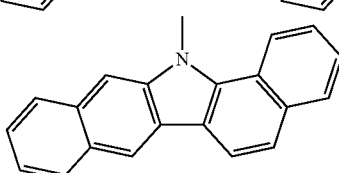

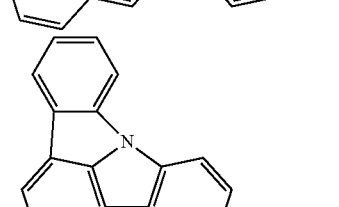

The alkyl group having 1 to 30 carbon atoms in the exemplary embodiment may be linear, branched or cyclic.

Examples of the linear or branched alkyl group are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neo-pentyl group, amyl group, isoamyl group, 1-methylpentyl group, 2-methylpentyl group, 1-pentylhexyl group, 1-butylpentyl group, 1-heptyloctyl group and 3-methylpentyl group.

The linear or branched alkyl group in the exemplary embodiment preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group and neopentyl group are particularly preferable.

Examples of the cycloalkyl group in the exemplary embodiment are a cyclopropyl group, cyclobutyl group, cyclopentyl group, cyclohexyl group, 4-metylcyclohexyl group, adamantyl group and norbornyl group. The cycloalkyl group preferably has 3 to 10 ring carbon atoms, more preferably 5 to 8 ring carbon atoms. Among the cycloalkyl group, a cyclopentyl group and a cyclohexyl group are particularly preferable.

A halogenated alkyl group provided by substituting an alkyl group with a halogen atom is exemplified by one provided by substituting an alkyl group having 1 to 30 carbon atoms with one or more halogen groups. Specific examples of the above halogenated alkyl group are a fluoromethyl group, difluoromethyl group, trifluoromethyl group, fluoroethyl group, trifluoromethylmethyl group, trifluoroethyl group and pentafluoroethyl group.

The alkylsilyl group having 3 to 30 carbon atoms in the exemplary embodiment is exemplified by a trialkylsilyl group having the above examples of the alkyl group having 1 to 30 carbon atoms. Specific examples of the alkylsilyl group are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups in the trialkylsilyl group may be the same or different.

Examples of the arylsilyl group having 6 to 30 ring carbon atoms in the exemplary embodiment are a dialkylarylsilyl group, alkyldiarylsilyl group and triarylsilyl group.

The dialkylarylsilyl group is exemplified by a dialkylarylsilyl group including two of the alkyl group listed as the examples of the alkyl group having 1 to 30 carbon atoms and one of the aryl group listed as the examples of the aryl group having 6 to 30 ring carbon atoms. The dialkylarylsilyl group preferably has 8 to 30 carbon atoms.

The alkyldiarylsilyl group is exemplified by an alkyldiarylsilyl group including one of the alkyl group listed as the examples of the alkyl group having 1 to 30 carbon atoms and two of the aryl group listed as the examples of the aryl group having 6 to 30 ring carbon atoms. The alkyldiarylsilyl group preferably has 13 to 30 carbon atoms.

The triarylsilyl group is exemplified by a triarylsilyl group including three of the aryl group listed as the examples of the aryl group having 6 to 30 ring carbon atoms. The triarylsilyl group preferably has 18 to 30 carbon atoms.

The alkoxy group having 1 to 30 carbon atoms in the exemplary embodiment is represented by $-OZ_1$. $Z_1$ is exemplified by the above alkyl group having 1 to 30 carbon atoms. Examples of the alkoxy group are a methoxy group, ethoxy group, propoxy group, butoxy group, pentyloxy group and hexyloxy group.

A halogenated alkoxy group provided by substituting an alkoxy group with a halogen atom is exemplified by one provided by substituting an alkoxy group having 1 to 30 carbon atoms with one or more halogen groups.

The aryloxy group having 6 to 30 ring carbon atoms in the exemplary embodiment is represented by $-OZ_2$. $Z_2$ is exemplified by the above aryl group having 6 to 30 ring carbon atoms. The aryloxy group is exemplified by a phenoxy group.

The alkylamino group having 2 to 30 carbon atoms is represented by $-NHRV$ or $-N(RV)2$. RV is exemplified by the alkyl group having 1 to 30 carbon atoms.

The arylamino group having 6 to 60 ring carbon atoms is represented by $-NHRW$ or $-N(RW)2$. RW is exemplified by the above aryl group having 6 to 30 ring carbon atoms.

The alkylthio group having 1 to 30 carbon atoms is represented by $-SRV$. RV is exemplified by the alkyl group having 1 to 30 carbon atoms.

The arylthio group having 6 to 30 ring carbon atoms is represented by $-SRW$. RW is exemplified by the above aryl group having 6 to 30 ring carbon atoms.

Herein, "carbon atoms forming a ring (ring carbon atoms)" mean carbon atoms forming a saturated ring, an unsaturated ring, or an aromatic ring. "Atoms forming a ring (ring atoms)" mean carbon atoms and hetero atoms forming a hetero ring including a saturated ring, unsaturated ring, or aromatic ring.

Herein, a hydrogen atom includes isotope having different numbers of neutrons, specifically, protium, deuterium and tritium.

Examples of the substituent meant by "substituted or unsubstituted" include alkenyl group, alkynyl group, halogen atom, cyano group, hydroxyl group, nitro group and carboxy group in addition to the above-described aryl group, heterocyclic group, alkyl group (linear or branched alkyl group, cycloalkyl group and haloalkyl group), alkylsilyl group, arylsilyl group, alkoxy group, aryloxy group, alkyl amino group, aryl amino group, alkylthio group, and arylthio group.

Among the above substituents, an aryl group, heterocyclic group, alkyl group, halogen atom, alkylsilyl group, arylsilyl group and cyano group are preferable. More preferable substituents are one listed as the preferable substituents described for each substituent.

The substituents may be further substituted by the aforementioned substituents. In addition, adjacent two or more of the substituents may be bonded to each other to form a ring.

The alkenyl group preferably has 2 to 30 carbon atoms and may be linear, branched or cyclic. Examples of the alkenyl group include a vinyl group, propenyl group, butenyl group, oleyl group, eicosapentaenyl group, docosahexaenyl group, styryl group, 2,2-diphenylvinyl group, 1,2,2-triphenylvinyl group, 2-phenyl-2-propenyl group, cyclopentadienyl group, cyclopentenyl group, cyclohexenyl group and cyclohexadienyl group.

The alkynyl group preferably has 2 to 30 carbon atoms and may be linear, branched or cyclic. Examples of the alkynyl group are ethynyl, propynyl and 2-phenylethynyl.

The aralkyl group preferably has 6 to 30 ring carbon atoms and is represented by $-Z_3-Z_4$. $Z_3$ is exemplified by an alkylene group corresponding to the above alkyl group having 1 to 30 carbon atoms. $Z_4$ is exemplified by the above aryl group having 6 to 30 ring carbon atoms. The aralkyl group is preferably an aralkyl group having 7 to 30 carbon atoms, in which an aryl portion has 6 to 30 carbon atoms, preferably 6 to 20 carbon atoms, more preferably 6 to 12 carbon atoms, and an alkyl portion has 1 to 30 carbon atoms, preferably 1 to 20 carbon atoms, more preferably 1 to 10 carbon atoms, further preferably 1 to 6 carbon atoms. Examples of the aralkyl group are a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

Examples of the halogen atom include a fluorine atom, a chlorine atom, a bromine atom and a iodine atom, among which a fluorine atom is preferable.

"Unsubstituted" in "substituted or unsubstituted" means that a group is not substituted by the above-described substituents but bonded with a hydrogen atom.

Herein, "XX to YY carbon atoms" in the description of "substituted or unsubstituted ZZ group having XX to YY carbon atoms" represent carbon atoms of an unsubstituted ZZ group and does not include carbon atoms of a substituted ZZ group. Here, "YY" is larger than "XX." Each of "XX" and "YY" represents an integer of 1 or more.

Herein, "XX to YY atoms" in the description of "substituted or unsubstituted ZZ group having XX to YY atoms" represent atoms of an unsubstituted ZZ group and does not include atoms of a substituted ZZ group. Here, "YY" is larger than "XX." Each of "XX" and "YY" represents an integer of 1 or more.

The same description as the above applies to "substituted or unsubstituted" in the following compound or a partial structure thereof.

In the exemplary embodiment, when the substituents are bonded to each other to form a ring structure, the ring structure is in a form of a saturated ring, unsaturated ring, or an aromatic ring.

Electronic Device

The organic EL device 1 according to the exemplary embodiment of the invention is usable for an electronic device such as a display device and a light-emitting device. Examples of the display device include a display component such as an organic EL panel module, TV, mobile phone, tablet and personal computer. Examples of the light-emitting device include an illuminator and a vehicle light.

Modification of Embodiment(s)

It should be noted that the invention is not limited to the above exemplary embodiment but may include any modification and improvement as long as such modification and improvement are compatible with the invention.

For instance, the emitting layer is not limited to a single layer, but may be provided by laminating a plurality of emitting layers. When the organic EL device has a plurality of emitting layers, it is only required that at least one of the emitting layers contains the first compound, the second compound and the third compound. For instance, the rest of the emitting layers may be a fluorescent emitting layer or a phosphorescent emitting layer with use of emission caused by electron transfer from the triplet excited state directly to the ground state.

When the organic EL device includes the plurality of emitting layers, the plurality of emitting layers may be adjacent to each other, or provide a so-called tandem-type organic EL device in which a plurality of emitting units are layered through an intermediate layer.

For instance, a blocking layer may be provided adjacent to the emitting layer closer to the anode and/or closer to the cathode. The blocking layer preferably abuts on the emitting layer and blocks at least one of holes, electrons and excitons.

For instance, when the blocking layer is provided abutting on the side of the emitting layer closer to the cathode, the blocking layer transports the electrons and blocks the holes from reaching a layer (e.g., the electron transporting layer) closer to the cathode beyond the blocking layer. When the organic EL device includes the electron transporting layer, the organic EL device preferably includes the blocking layer between the emitting layer and the electron transporting layer.

When the blocking layer is provided abutting on the side of the emitting layer closer to the anode, the blocking layer transports the holes and blocks the electrons from reaching a layer (e.g., the hole transporting layer) closer to the anode beyond the blocking layer. When the organic EL device includes the hole transporting layer, the organic EL device preferably includes the blocking layer between the emitting layer and the hole transporting layer.

Moreover, the blocking layer may abut on the emitting layer so that excited energy does not leak out from the emitting layer toward neighboring layer(s). Accordingly, the blocking layer blocks excitons generated in the emitting layer from transferring to a layer(s) (e.g., the electron transporting layer and the hole transporting layer) closer to the electrode(s) beyond the blocking layer.

The emitting layer and the blocking layer preferably abut on each other.

In addition, the specific structure and shapes for practicing the invention may be altered to other structures and shapes as long as such other structures and shapes are compatible with the invention.

EXAMPLES

Next, Examples will be described. However, the invention is by no means limited by these Examples.

Compounds used for manufacturing an organic EL device will be shown below.

[Formula 41]

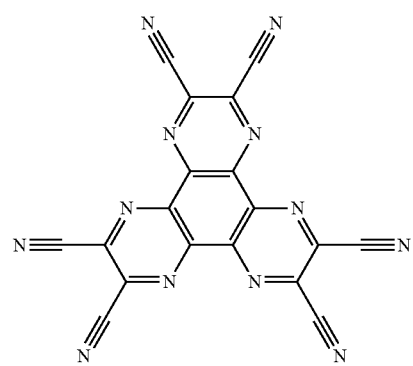

HI

HT-1
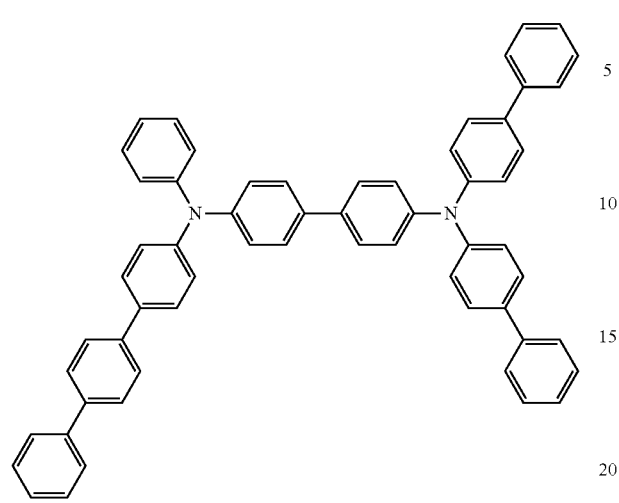
BH-3
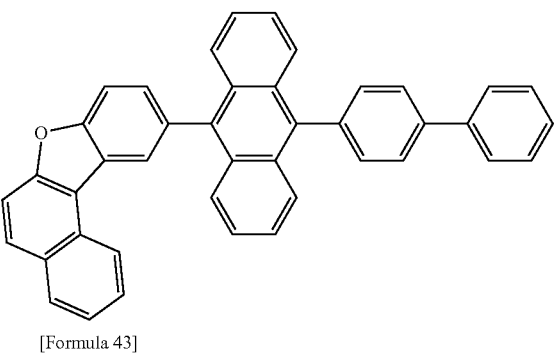
[Formula 43]
BH-4
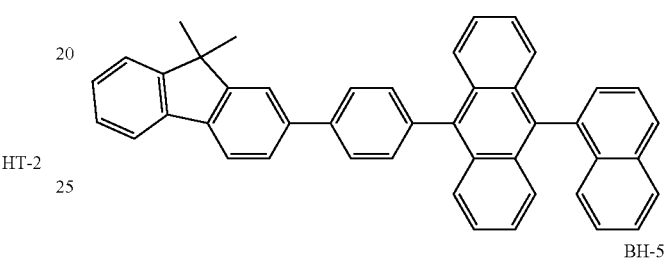
HT-2
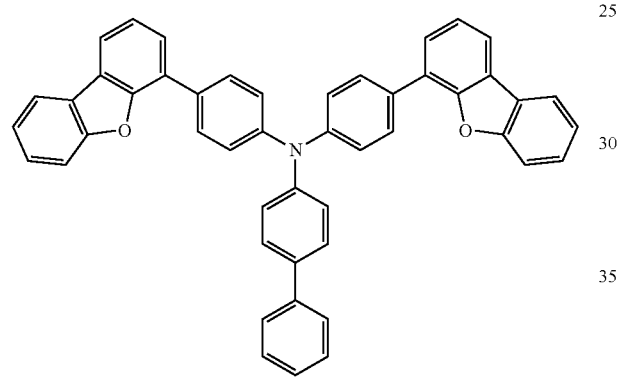
BH-5
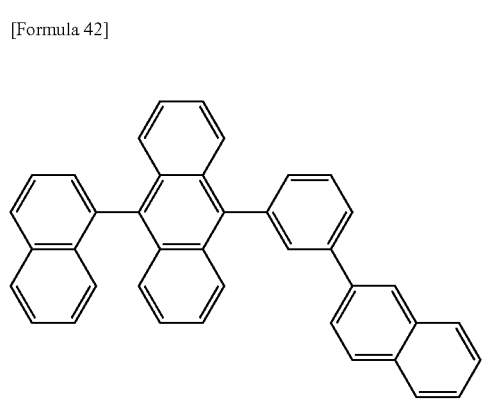
[Formula 42]
BH-1
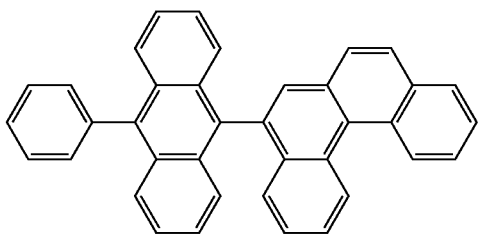
BH-6
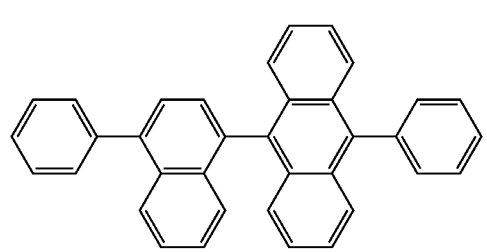
[Formula 44]
BH-7
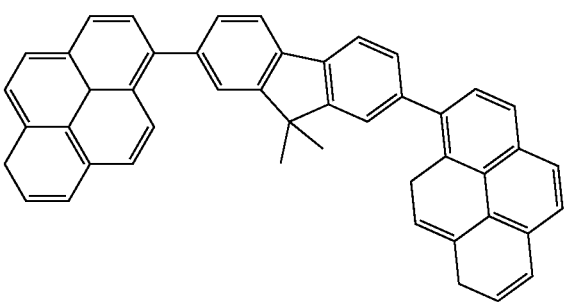
BH-2

-continued

[Formula 45]

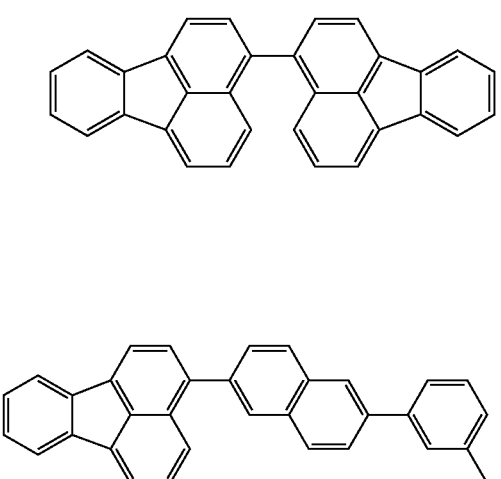

CH-1

CH-2

CH-3

[Formula 46]

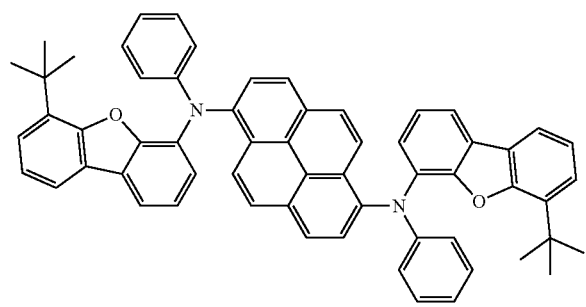

BD-1

-continued

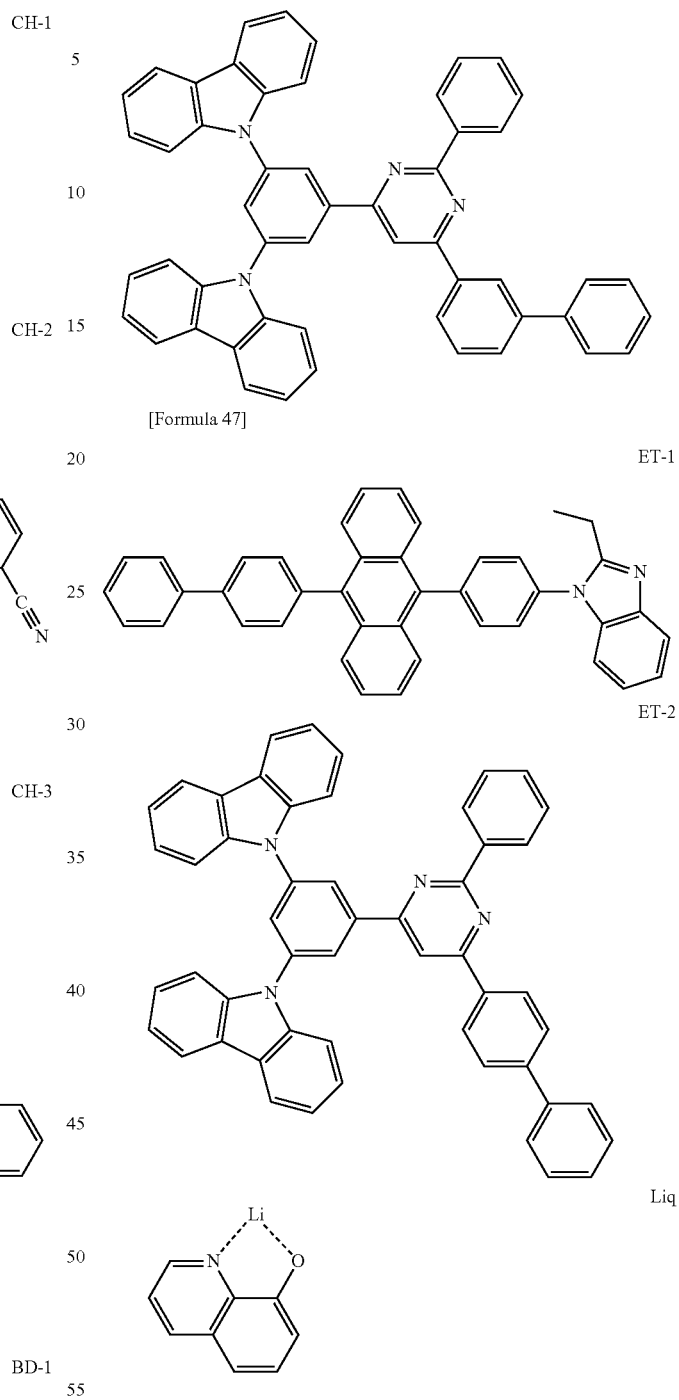

HB-1

[Formula 47]

ET-1

ET-2

Liq

Evaluation of Compounds

Next, properties of the compounds used in Example were measured. A measurement method and a calculation method are described below. Measurement results or calculation results are shown in Table 1.

Singlet Energy S

Singlet energy S is measured as follows.

A 10 μmol/L toluene solution of a measurement target compound was prepared and put in a quartz cell. An absorption spectrum (ordinate axis: luminous intensity, abscissa axis: wavelength) of the thus-obtained sample was measured at a normal temperature (300K). A tangent was drawn to the fall of the absorption spectrum on the long-wavelength side, and a wavelength value λedge (nm) at an intersection of the tangent and the abscissa axis was assigned to a conversion equation 1 below to calculate singlet energy.

$$S\,(eV)=1239.85/\lambda edge \qquad \text{Conversion equation 1:}$$

In Examples, the absorption spectrum was measured using a spectrophotometer (U3310 manufactured by Hitachi, Ltd.).

The tangent to the fall of the absorption spectrum on the long-wavelength side was drawn as follows. While moving on a curve of the absorption spectrum from the maximum spectral value closest to the long-wavelength side in a long-wavelength direction, a tangent at each point on the curve was checked. An inclination of the tangent was decreased and increased in a repeated manner as the curve fell (i.e., a value of the ordinate axis was decreased). A tangent drawn at a point of the minimum inclination closest to the long-wavelength side (except when absorbance was 0.1 or less) was defined as the tangent to the fall of the absorption spectrum on the long-wavelength side.

The maximum absorbance of 0.2 or less was not included in the above-mentioned maximum absorbance on the long-wavelength side.

Triplet Energy T

The triplet energy was measured as follows. The measurement target compound was dissolved in EPA (diethylether:isopentane:ethanol =5:5:2 in volume ratio) at a concentration of 10 μmol/L. The obtained solution was put into a quartz cell to provide a measurement sample. A phosphorescent spectrum (ordinate axis: phosphorescent luminous intensity, abscissa axis: wavelength) of the measurement sample was measured at a low temperature (77K). A tangent was drawn to the rise of the phosphorescent spectrum on the short-wavelength side. The triplet energy was calculated by a conversion equation 2 below based on a wavelength value λedge (nm) at an intersection of the tangent and the abscissa axis.

$$T\,(eV)=1239.85/\lambda edge \qquad \text{Conversion equation 2:}$$

For phosphorescence measurement, a spectrophotofluorometer body F-4500(manufactured by Hitachi High-Technologies Corporation) was used.

The tangent to the rise of the phosphorescence spectrum on the short-wavelength side was drawn as follows. While moving on a curve of the phosphorescence spectrum from the short-wavelength side to the maximum spectral value closest to the short-wavelength side among the maximum spectral values, a tangent was checked at each point on the curve toward the long-wavelength of the phosphorescence spectrum. An inclination of the tangent was increased as the curve rises (i.e., a value of the ordinate axis was increased). A tangent drawn at a point of the maximum inclination (i.e., a tangent at an inflection point) was defined as the tangent to the rise of the phosphorescence spectrum on the short-wavelength side.

The maximum with peak intensity being 15% or less of the maximum peak intensity of the spectrum was not included in the above-mentioned maximum closest to the short-wavelength side of the spectrum. The tangent drawn at a point of the maximum spectral value being closest to the short-wavelength side and having the maximum inclination was defined as a tangent to the rise of the phosphorescence spectrum on the short-wavelength side.

Ionization Potential Ip

A photoelectron spectroscopy (AC-3, manufactured by Riken Keiki Co., Ltd.) was used for the measurement under atmosphere. Specifically, the measurement target compound was irradiated with light and the amount of electrons generated by charge separation was measured.

Electron Affinity Af

The electron affinity was calculated in accordance with a conversion equation below using the respective measurement values of the ionization potential Ip and the singlet energy S of the compounds measured by the above method.

$$Af=Ip-S$$

TABLE 1

| Compound | S (eV) | T (eV) | Ip (eV) | Af (eV) |
|---|---|---|---|---|
| BH-1 | 3.0 | 1.8 | 6.0 | 3.0 |
| BH-2 | 3.0 | 1.8 | 6.0 | 3.0 |
| BH-3 | 3.0 | 1.8 | 5.9 | 2.9 |
| BH-4 | 3.0 | 1.8 | 5.8 | 2.8 |
| BH-5 | 3.0 | 1.8 | 5.9 | 2.9 |
| BH-6 | 3.0 | 1.8 | 6.0 | 3.0 |
| BH-7 | 3.1 | 2.2 | 5.9 | 2.8 |
| CH-1 | 3.0 | 2.3 | 6.4 | 3.5 |
| CH-2 | 3.0 | 2.2 | 6.3 | 3.3 |
| CH-3 | 3.1 | 2.3 | 6.2 | 3.1 |
| BD-1 | 2.8 | 2.1 | 5.6 | 2.8 |

Manufacturing Examples of Organic EL Device

Example 1

A glass substrate (size: 25 mm×75 mm×1.1 mm thick) having an ITO transparent electrode (manufactured by GEOMATEC Co., Ltd.) was ultrasonic-cleaned in isopropyl alcohol for five minutes, and then UV/ozone-cleaned for 30 minutes. A thickness of ITO transparent electrode was 130 nm.

After the glass substrate having the ITO transparent electrode line was cleaned, the glass substrate was mounted on a substrate holder of a vacuum evaporation apparatus. Initially, a compound HI was deposited on a surface of the glass substrate where the ITO transparent electrode line was provided in a manner to cover the transparent electrode, thereby forming a 10-nm thick HI film as a hole injecting layer.

Next, a compound HT-1 as a hole transporting material was deposited on the HI film to form a 80-nm thick HT-1 film as a first hole transporting layer.

Subsequently, a compound HT-2 as a second hole transporting material was deposited on the HT-1 film to form a 10-nm thick HT-2 film as a second hole transporting layer.

Further, a compound BH-1 (the first compound), a compound CH-1 (the second compound) and a compound BD-1 (the third compound) were co-deposited on the HT-2 film. Thus, a 25-nm thick emitting layer was formed. In the emitting layer, a ratio of the compound BH-1 was set at 92 mass %, a ratio of the compound CH-1 was set at 4 mass %, and a ratio of the compound BD-1 was set at 4 mass %.

A compound HB-1 was deposited on the emitting layer to form a 25-nm HB-1 film as a hole blocking layer.

Next, a compound ET-1 was deposited on the HB-1 film to form a 10-nm thick electron transporting layer.

Next, LiF was deposited on the electron transporting layer at a film formation speed of 0.1 angstrom/min to form a 1-nm thick LiF film as an electron-injecting electrode (cathode).

A metal Al was deposited on the LiF film to form an 80-nm thick metal Al cathode.

A device arrangement of the organic EL device in Example 1 is schematically shown as follows.

ITO(130)/HI(10)/HT-1(80)/HT-2(10)/BH-1:CH-1:BD-1 (25, 92%:4%:4%)/HB-1(25)/ET-1(10)/LiF(1)/Al(80)

Numerals in parentheses represent a film thickness (unit: nm). The numerals represented by percentage in parentheses indicate a ratio (mass %) of each of the materials of the emitting layer.

Example 2

The organic EL device of Example 2 was prepared in the same manner as the organic EL device of Example 1 until the emitting layer was formed, and subsequently by co-depositing a compound ET-2 and Liq(8-quinolinolato-lithium). Thus, a 36-nm thick electron transporting layer was formed. In the electron transporting layer, a ratio of the compound ET-2 was set at 50 mass % and a ratio of Liq was set at 50 mass %.

Next, LiF was deposited on the electron transporting layer to form a 1-nm thick LiF film as an electron-injecting electrode (cathode).

A metal Al was deposited on the LiF film to form an 80-nm thick metal Al cathode.

A device arrangement of the organic EL device in Example 2 is schematically shown as follows.

ITO(130)/HI(10)/HT-1(80)/HT-2(10)/BH-1:CH-1:BD-1 (25, 92%:4%:4%)/ET-2:Liq(36, 50%:50%)/Liq(1)/Al(80)

Comparative 1

An organic EL device in Comparative 1 was manufactured in the same manner as in Example 1 except that the compound BH-1 and the compound BD-1 were co-deposited to form a 25-nm thick emitting layer in place of the emitting layer in Example 1. In the emitting layer, the ratio of the compound BH-1 was set at 96 mass % and the ratio of the compound BD-1 was set at 4 mass %.

A device arrangement of the organic EL device in Comparative 1 is schematically shown as follows.

ITO(130)/HI(10)/HT-1(80)/HT-2(10)/BH-1:BD-1(25, 96%:4%)/HB-1(25)/ET-1(10)/LiF(1)/Al(80)

Comparative 2

An organic EL device in Comparative 2 was manufactured in the same manner as in Example 2 except that the compound BH-1 and the compound BD-1 were co-deposited to form a 25-nm thick emitting layer in place of the emitting layer in Example 2. In the emitting layer, the ratio of the compound BH-1 was set at 96 mass % and the ratio of the compound BD-1 was set at 4 mass %.

A device arrangement of the organic EL device in Comparative 2 is schematically shown as follows.

ITO(130)/HI(10)/HT-1(80)/HT-2(10)/BH-1:BD-1(25, 96%:4%)/ET-2:Liq(36, 50%:50%)/Liq(1)/Al(80)

Comparative 3

An organic EL device in Comparative 3 was manufactured in the same manner as in Example 1 except that the compound BH-1, a compound CH-3 and the compound BD-1 were co-deposited to form a 25-nm thick emitting layer in place of the emitting layer in Example 1. In the emitting layer, the ratio of the compound BH-1 was set at 92 mass %, a ratio of the compound CH-3 was set at 4 mass %, and the ratio of the compound BD-1 was set at 4 mass %.

A device arrangement of the organic EL device in Comparative 3 is schematically shown as follows.

ITO(130)/HI(10)/HT-1(80)/HT-2(10)/BH-1:CH-3:BD-1 (25, 92%:4%:4%)/HB-1(25)/ET-1(10)/LiF(1)/Al(80)

Comparative 4

An organic EL device in Comparative 4 was manufactured in the same manner as in Example 1 except that a compound BH-7, the compound CH-1 and the compound BD-1 were co-deposited to form a 25-nm thick emitting layer in place of the emitting layer in Example 1. In the emitting layer, a ratio of the compound BH-7 was set at 92 mass %, the ratio of the compound CH-1 was set at 4 mass %, and the ratio of the compound BD-1 was set at 4 mass %.

A device arrangement of the organic EL device in Comparative 4 is schematically shown as follows.

ITO(130)/HI(10)/HT-1(80)/HT-2(10)/BH-7:CH-1:BD-1 (25, 92%:4%:4%)/HB-1(25)/ET-1(10)/LiF(1)/Al(80)

Evaluation of Organic EL Devices

The organic EL devices manufactured in Examples 1 to 2 and Comparatives 1 to 4 were evaluated as follows. The evaluation results are shown in Tables 2 and 3.

CIE1931 Chromaticity

Voltage was applied on each of the organic EL devices such that a current density was 10 mA/cm$^2$, where coordinates (x, y) of CIE1931 chromaticity were measured by a spectroradiometer (CS-1000 manufactured by Konica Minolta, Inc.).

Main Peak Wavelength $\lambda_p$

Voltage was applied on each of the organic EL devices such that a current density was 10 mA/cm$^2$, where spectral radiance spectrum was measured by the above spectroradiometer and a main peak wavelength $\lambda_p$ (unit: nm) was read from the obtained spectral radiance spectrum.

Lifetime LT80

A voltage was applied on each of the organic EL devices such that a current density was 50 mA/cm$^2$, where a time (unit: hrs) elapsed before a luminance intensity was reduced to 80% of the initial luminance intensity was measured as a lifetime LT80.

TABLE 2

| | Emitting Layer | | | Chromaticity | | $\lambda_p$ | LT80 |
|---|---|---|---|---|---|---|---|
| | M1 | M2 | M3 | x | y | (nm) | (hrs) |
| Example 1 | BH-1 | CH-1 | BD-1 | 0.138 | 0.106 | 457 | 480 |
| Comparative 1 | BH-1 | — | BD-1 | 0.136 | 0.100 | 457 | 350 |
| Comparative 3 | BH-1 | CH-3 | BD-1 | 0.134 | 0.108 | 458 | 300 |
| Comparative 4 | CH-7 | CH-1 | BD-1 | 0.147 | 0.149 | 460 | 140 |

TABLE 3

| | Emitting Layer | | | Chromaticity | | $\lambda_p$ | LT80 |
|---|---|---|---|---|---|---|---|
| | M1 | M2 | M3 | x | y | (nm) | (hrs) |
| Example 2 | BH-1 | CH-1 | BD-1 | 0.137 | 0.113 | 458 | 350 |
| Comparative 2 | BH-1 | — | BD-1 | 0.135 | 0.104 | 458 | 300 |

Since the organic EL device in Example 1 included the emitting layer containing the compound BH-1 (the first compound), the compound CH-1 (the second compound), and the compound BD-1 (the third compound) which satisfied the relationships of the numerical formulae (Numerical Formula 1) to (Numerical Formula 3), the organic EL device in Example 1 exhibited a longer lifetime than those of the organic EL devices in Comparatives 1, 3 and 4.

It is deduced that the organic EL device in Comparative 1 exhibited a shorter lifetime than in Example 1 because of the emitting layer formed of the compound BH-1 and the compound BD-1.

It is deduced that the organic EL device in Comparative 3 exhibited a shorter lifetime because the numerical formula (2) was not satisfied since Af (affinity) of the compound CH-3 was 3.1 eV.

It is deduced that the organic EL device in Comparative 4 exhibited a shorter lifetime because the numerical formula (3) was not satisfied since the triplet energy T(M1) of the compound BH-7 was 2.2 eV.

Since the organic EL device in Example 2 included the emitting layer containing the compound BH-1 (the first compound), the compound CH-1 (the second compound), and the compound BD-1 (the third compound) which satisfied the relationships of the numerical formulae (Numerical Formula 1) to (Numerical Formula 3), the organic EL device in Example 2 exhibited a longer lifetime than that of the organic EL device in Comparative 2. It is deduced that the organic EL device in Comparative 2 exhibited a shorter lifetime than in Example 2 because of the emitting layer formed by the compound BH-1 and the compound BD-1.

Manufacturing Examples of Organic EL Device

Example 3

An organic EL device in Example 3 was manufactured in the same manner as in Example 1 except that the compound BH-1 was replaced by the compound BH-2 and the compound CH-1 was replaced by a compound CH-2 in the emitting layer of Example 1.

A device arrangement of the organic EL device in Example 3 is schematically shown as follows.

ITO(130)/HI(10)/HT-1(80)/HT-2(10)/BH-2:CH-2:BD-1 (25, 92%:4%:4%)/HB-1(25)/ET-1(10)/LiF(1)/Al(80)

Comparative 5

An organic EL device in Comparative 5 was manufactured in the same manner as in Example 1 except that the compound BH-2 and the compound BD-1 were co-deposited to form a 25-nm thick emitting layer in place of the emitting layer in Example 1. In the emitting layer, the ratio of the compound BH-2 was set at 96 mass % and the ratio of the compound BD-1 was set at 4 mass %.

A device arrangement of the organic EL device in Comparative 5 is schematically shown as follows.

ITO(130)/HI(10)/HT-1(80)/HT-2(10)/BH-2:BD-1(25, 96%:4%)/HB-1(25)/ET-1(10)/LiF(1)/Al(80)

Evaluation of Organic EL Devices

The organic EL devices manufactured in Example 3 and Comparative 5 were evaluated in the same manner as described above. The evaluation results are shown in Table 4.

TABLE 4

| | Emitting Layer | | | Chromaticity | | $\lambda_p$ | LT80 |
|---|---|---|---|---|---|---|---|
| | M1 | M2 | M3 | x | y | (nm) | (hrs) |
| Example 3 | BH-2 | CH-2 | BD-1 | 0.137 | 0.101 | 456 | 250 |
| Comparative 5 | BH-2 | — | BD-1 | 0.136 | 0.095 | 455 | 210 |

Since the organic EL device in Example 3 included the emitting layer containing the compound BH-2 (the first compound), the compound CH-2 (the second compound), and the compound BD-1 (the third compound) which satisfied the relationships of the numerical formulae (Numerical Formula 1) to (Numerical Formula 3), the organic EL device in Example 3 exhibited a longer lifetime than that of the organic EL device in Comparative 5. It is deduced that the organic EL device in Comparative 5 exhibited a shorter lifetime than in Example 3 because of the emitting layer formed by the compound BH-2 and the compound BD-1.

Manufacturing Examples of Organic EL Device

Example 4

An organic EL device in Example 4 was manufactured in the same manner as in Example 1 except that the compound BH-1 was replaced by a compound BH-3 in the emitting layer of Example 1.

A device arrangement of the organic EL device in Example 4 is schematically shown as follows.

ITO(130)/HI(10)/HT-1(80)/HT-2(10)/BH-3:CH-1:BD-1 (25, 92%:4%:4%)/HB-1(25)/ET-1(10)/LiF(1)/Al(80)

Example 5

An organic EL device in Example 5 was manufactured in the same manner as in Example 2 except that the compound BH-1 was replaced by the compound BH-3 in the emitting layer of Example 2.

A device arrangement of the organic EL device in Example 5 is schematically shown as follows.

ITO(130)/HI(10)/HT-1(80)/HT-2(10)/BH-3:CH-1:BD-1 (25, 92%:4%:4%)/ET-2:Liq(36, 50%:50%)/Liq(1)/Al(80)

Example 6

An organic EL device in Example 6 was manufactured in the same manner as in Example 4 except that the compound CH-1 was replaced by the compound CH-2 in the emitting layer of Example 4.

A device arrangement of the organic EL device in Example 6 is schematically shown as follows.

ITO(130)/HI(10)/HT-1(80)/HT-2(10)/BH-3:CH-2:BD-1 (25, 92%:4%:4%)/HB-1(25)/ET-1(10)/LiF(1)/Al(80)

Comparative 6

An organic EL device in Comparative 6 was manufactured in the same manner as in Example 1 except that the compound BH-3 and the compound BD-1 were co-deposited to form a 25-nm thick emitting layer in place of the emitting layer in Example 1. In the emitting layer, the ratio of the compound BH-3 was set at 96 mass % and the ratio of the compound BD-1 was set at 4 mass %.

A device arrangement of the organic EL device in Comparative 6 is schematically shown as follows.

ITO(130)/HI(10)/HT-1(80)/HT-2(10)/BH-3:BD-1(25, 96%:4%)/HB-1(25)/ET-1(10)/LiF(1)/Al(80)

Comparative 7

An organic EL device in Comparative 7 was manufactured in the same manner as in Example 2 except that the compound BH-3 and the compound BD-1 were co-deposited to form a 25-nm thick emitting layer in place of the emitting layer in Example 2. In the emitting layer, the ratio of the compound BH-3 was set at 96 mass % and the ratio of the compound BD-1 was set at 4 mass %.

A device arrangement of the organic EL device in Comparative 7 is schematically shown as follows.

ITO(130)/HI(10)/HT-1(80)/HT-2(10)/BH-3:BD-1(25, 96%:4%)/ET-2:Liq(36, 50%:50%)/Liq(1)/Al(80)

Evaluation of Organic EL Devices

The organic EL devices manufactured in Examples 4 to 6 and Comparatives 6 and 7 were evaluated in the same manner as described above. The evaluation results are shown in Tables 5 and 6.

TABLE 5

| | Emitting Layer | | | Chromaticity | | $\lambda_p$ | LT80 |
|---|---|---|---|---|---|---|---|
| | M1 | M2 | M3 | x | y | (nm) | (hrs) |
| Example 4 | BH-3 | CH-1 | BD-1 | 0.138 | 0.108 | 458 | 600 |
| Example 6 | BH-3 | CH-2 | BD-1 | 0.137 | 0.107 | 458 | 442 |
| Comparative 6 | BH-3 | — | BD-1 | 0.138 | 0.098 | 457 | 328 |

TABLE 6

| | Emitting Layer | | | Chromaticity | | $\lambda_p$ | LT80 |
|---|---|---|---|---|---|---|---|
| | M1 | M2 | M3 | x | y | (nm) | (hrs) |
| Example 5 | BH-3 | CH-1 | BD-1 | 0.137 | 0.114 | 458 | 460 |
| Comparative 7 | BH-3 | — | BD-1 | 0.136 | 0.105 | 458 | 370 |

Since the organic EL devices in Examples 4 and 6 included the emitting layer containing the first compound, the second compound, and the third compound which satisfied the relationships of the numerical formulae (Numerical Formula 1) to (Numerical Formula 3), the organic EL devices in Examples 4 and 6 exhibited a longer lifetime than that of the organic EL device in Comparative 6. It is deduced that the organic EL device in Comparative 6 exhibited a shorter lifetime than in Examples 4 and 6 because of the emitting layer formed by the compound BH-3 and the compound BD-1.

Since the organic EL device in Example 5 included the emitting layer containing the first compound, the second compound, and the third compound which satisfied the relationships of the numerical formulae (Numerical Formula 1) to (Numerical Formula 3), the organic EL device in Example 5 exhibited a longer lifetime than that of the organic EL device in Comparative 7. It is deduced that the organic EL device in Comparative 7 exhibited a shorter lifetime than in Example 5 because of the emitting layer formed by the compound BH-3 and the compound BD-1.

Manufacturing Examples of Organic EL Device

Example 7

An organic EL device in Example 7 was manufactured in the same manner as in Example 1 except that the compound BH-1 was replaced by a compound BH-5 and the compound CH-1 was replaced by the compound CH-2 in the emitting layer of Example 1.

A device arrangement of the organic EL device in Example 7 is schematically shown as follows.

ITO(130)/HI(10)/HT-1(80)/HT-2(10)/BH-5:CH-2:BD-1 (25, 92%:4%:4%)/HB-1(25)/ET-1(10)/LiF(1)/Al(80)

Comparative 8

An organic EL device in Comparative 8 was manufactured in the same manner as in Example 1 except that the compound BH-5 and the compound BD-1 were co-deposited to form a 25-nm thick emitting layer in place of the emitting layer in Example 1. In the emitting layer, a ratio of the compound BH-5 was set at 96 mass % and the ratio of the compound BD-1 was set at 4 mass %.

A device arrangement of the organic EL device in Comparative 8 is schematically shown as follows.

ITO(130)/HI(10)/HT-1(80)/HT-2(10)/BH-5:BD-1(25, 96%:4%)/HB-1(25)/ET-1(10)/LiF(1)/Al(80)

Evaluation of Organic EL Devices

The organic EL devices manufactured in Example 7 and Comparative 8 were evaluated in the same manner as described above. The evaluation results are shown in Table 7.

TABLE 7

| | Emitting Layer | | | Chromaticity | | $\lambda_p$ | LT80 |
|---|---|---|---|---|---|---|---|
| | M1 | M2 | M3 | x | y | (nm) | (hrs) |
| Example 7 | BH-5 | CH-2 | BD-1 | 0.135 | 0.113 | 458 | 250 |
| Comparative 8 | BH-5 | — | BD-1 | 0.135 | 0.105 | 458 | 150 |

Since the organic EL device in Example 7 included the emitting layer containing the compound BH-5 (the first compound), the compound CH-2 (the second compound), and the compound BD-1 (the third compound) which satisfied the relationships of the numerical formulae (Numerical Formula 1) to (Numerical Formula 3), the organic EL device in Example 7 exhibited a longer lifetime than that of the organic EL device in Comparative 8. It is deduced that the organic EL device in Comparative 8 exhibited a shorter lifetime than in Example 7 because of the emitting layer formed by the compound BH-5 and the compound BD-1.

Manufacturing Examples of Organic EL Device

Example 8

An organic EL device in Example 8 was manufactured in the same manner as in Example 1 except that the compound BH-1 was replaced by a compound BH-6 and the compound CH-1 was replaced by the compound CH-2 in the emitting layer of Example 1.

A device arrangement of the organic EL device in Example 8 is schematically shown as follows.

ITO(130)/HI(10)/HT-1(80)/HT-2(10)/BH-6:CH-2:BD-1 (25, 92%:4%:4%)/HB-1(25)/ET-1(10)/LiF(1)/Al(80)

Comparative 9

An organic EL device in Comparative 9 was manufactured in the same manner as in Example 1 except that the compound BH-6 and the compound BD-1 were co-deposited to form a 25-nm thick emitting layer in place of the emitting layer in Example 1. In the emitting layer, a ratio of the compound BH-6 was set at 96 mass % and the ratio of the compound BD-1 was set at 4 mass %.

A device arrangement of the organic EL device in Comparative 9 is schematically shown as follows.

ITO(130)/HI(10)/HT-1(80)/HT-2(10)/BH-6:BD-1(25, 96%:4%)/HB-1(25)/ET-1(10)/LiF(1)/Al(80)

Evaluation of Organic EL Devices

The organic EL devices manufactured in Example 8 and Comparative 9 were evaluated in the same manner as described above. The evaluation results are shown in Table 8.

TABLE 8

| | Emitting Layer | | | Chromaticity | | $\lambda_p$ | LT80 |
| --- | --- | --- | --- | --- | --- | --- | --- |
| | M1 | M2 | M3 | x | y | (nm) | (hrs) |
| Example 8 | BH-6 | CH-2 | BD-1 | 0.135 | 0.113 | 458 | 250 |
| Comparative 9 | BH-6 | — | BD-1 | 0.134 | 0.110 | 458 | 210 |

Since the organic EL device in Example 8 included the emitting layer containing the compound BH-6 (the first compound), the compound CH-2 (the second compound), and the compound BD-1 (the third compound) which satisfied the relationships of the numerical formulae (Numerical Formula 1) to (Numerical Formula 3), the organic EL device in Example 8 exhibited a longer lifetime than that of the organic EL device in Comparative 9. It is deduced that the organic EL device in Comparative 9 exhibited a shorter lifetime than in Example 8 because of the emitting layer formed by the compound BH-6 and the compound BD-1.

The invention claimed is:

1. An organic electroluminescence device comprising:
   an anode;
   a cathode; and
   an emitting layer, wherein
   the emitting layer comprises a first compound, a second compound, and a third compound,
   a singlet energy S(M1) of the first compound and a singlet energy S(M2) of the second compound satisfy a relationship of Numerical Formula 1 below,
   an electron affinity Af(M1) of the first compound and an electron affinity Af(M2) of the second compound satisfy a relationship of Numerical Formula 2 below, and
   a triplet energy T(M1) of the first compound satisfies a relationship of Numerical Formula 3 below, $S(M2) \geq S(M1) \times 0.95$   (Numerical Formula 1)

$Af(M2) - Af(M1) \geq 0.2 eV$   (Numerical Formula 2)

$T(M1) \leq 2.0 eV$   (Numerical Formula 3).

2. The organic electroluminescence device according to claim 1, wherein
   the singlet energy S(M1) of the first compound and the singlet energy S(M2) of the second compound satisfy a relationship of Numerical Formula 4 below, $S(M2) \geq S(M1)$   (Numerical Formula 4).

3. The organic electroluminescence device according to claim 1, wherein
   the singlet energy S(M2) of the second compound satisfies a relationship of Numerical Formula 5 below, $S(M2) \geq 3.0 eV$   (Numerical Formula 5).

4. The organic electroluminescence device according to claim 1, wherein
   the electron affinity Af(M1) of the first compound and the electron affinity Af(M2) of the second compound satisfy a relationship of Numerical Formula 6 below, $Af(M2) - Af(M1) > 0.2 eV$   (Numerical Formula 6).

5. The organic electroluminescence device according to claim 1, wherein
   an ionization potential Ip(M3) of the third compound and an ionization potential Ip(M1) of the first compound satisfy a relationship of Numerical Formula 10 below, $Ip(M1) - Ip(M3) \geq 0.2 eV$   (Numerical Formula 10).

6. The organic electroluminescence device according to claim 1, wherein
   a singlet energy S(M3) of the third compound and the singlet energy S(M1) of the first compound satisfy a relationship of Numerical Formula 12 below, $S(M1) > S(M3)$   (Numerical Formula 12).

7. The organic electroluminescence device according to claim 1, wherein
   the triplet energy T(M1) of the first compound and a triplet energy T(M2) of the second compound satisfy a relationship of Numerical Formula 7 below, $T(M1) < T(M2)$   (Numerical Formula 7).

8. The organic electroluminescence device according to claim 7, wherein the third compound is a fluorescent material.

9. The organic electroluminescence device according to claim 1, wherein
   the first compound is represented by a formula (1) below,

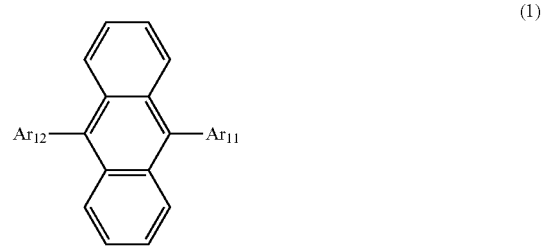

(1)

where: $Ar_{11}$ and $Ar_{12}$ are each independently a substituted or unsubstituted aromatic hydrocarbon group having 6 to 30 ring carbon atoms, or substituted or unsubstituted heterocyclic group having 5 to 30 ring atoms.

10. The organic electroluminescence device according to claim 9, wherein
    $Ar_{11}$ and $Ar_{12}$ are each independently a substituted or unsubstituted phenyl group.

11. The organic electroluminescence device according to claim 9, wherein
    $Ar_{11}$ is a substituted or unsubstituted naphthyl group and $Ar_{12}$ is a substituted or unsubstituted phenyl group.

12. The organic electroluminescence device according to claim 9, wherein
    $Ar_{11}$ is any one group selected from the group consisting of a substituted or unsubstituted phenanthryl group, substituted or unsubstituted benzoanthryl group, 9,9-dimethylfluorenyl group, 9,9-diphenylfluorenyl group, substituted or unsubstituted dibenzofuranyl group, substituted or unsubstituted dibenzothiophenyl group, substituted or unsubstituted naphthobenzofuranyl group, substituted or unsubstituted naphthobenzothiophenyl group, and substituted or unsubstituted naphthobenzofluorenyl group, and
    $Ar_{12}$ is a substituted or unsubstituted phenyl group or a substituted or unsubstituted naphthyl group.

13. The organic electroluminescence device according to claim 1, wherein
    the second compound is represented by a formula (21) below,

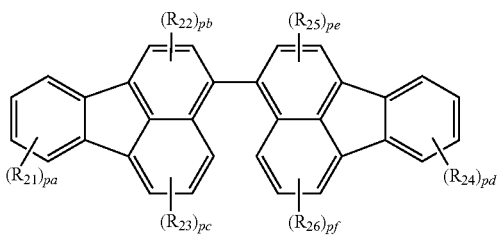

(21)

where: $R_{21}$ to $R_{26}$ are each independently a hydrogen atom or a substituent, and, when $R_{21}$ to $R_{26}$ are substituents, each of the substituents is a substituent selected from the group consisting of a halogen atom, a hydroxyl group, a cyano group, a substituted or unsubstituted alkyl group having 1 to 30 carbon atoms, a substituted or unsubstituted alkoxy group having 1 to 30 carbon atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a silyl group represented by -Si($R_{221}$)$_3$, an amino group represented by -N($R_{222}$)$_2$, a substituted or unsubstituted aromatic hydrocarbon group having 6 to 30 ring carbon atoms, and a substituted or unsubstituted heterocyclic group having 5 to 30 ring atoms;

$R_{221}$ is each independently a hydrogen atom or a substituent, and when $R_{221}$ is a substituent, the substituent is a substituted or unsubstituted alkyl group having 1 to 30 carbon atoms, or a substituted or unsubstituted aromatic hydrocarbon group having 6 to 30 ring carbon atoms;

a plurality of $R_{221}$ are mutually the same or different;

$R_{222}$ is each independently a hydrogen atom or a substituent, and when $R_{222}$ is a substituent, the substituent is a substituted or unsubstituted alkyl group having 1 to 30 carbon atoms, or a substituted or unsubstituted aromatic hydrocarbon group having 6 to 30 ring carbon atoms;

a plurality of $R_{222}$ are mutually the same or different;

pa is 4 and a plurality of $R_{21}$ are mutually the same or different;

pb is 2 and a plurality of $R_{22}$ are mutually the same or different;

pc is 3 and a plurality of $R_{23}$ are mutually the same or different;

pd is 4 and a plurality of $R_{24}$ are mutually the same or different;

pe is 2 and a plurality of $R_{25}$ are mutually the same or different;

pf is 3 and a plurality of $R_{26}$ are mutually the same or different; and each of $R_{21}$ to $R_{26}$ is bonded to a carbon atom of each of the aromatic rings.

14. The organic electroluminescence device according to claim 13, wherein
$R_{21}$ to $R_{26}$ are hydrogen atoms.

15. The organic electroluminescence device according to claim 1, wherein
the second compound is represented by a formula (22) below,

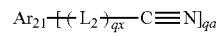

(22)

where: $Ar_{21}$ is a substituted or unsubstituted fused aromatic hydrocarbon group having 10 to 30 ring carbon atoms;

$L_2$ is a single bond or a linking group;

the linking group in $L_2$ is a substituted or unsubstituted aromatic hydrocarbon group having 6 to 30 ring carbon atoms, or a substituted or unsubstituted heterocyclic group having 5 to 30 ring atoms;

qx is an integer from 1 to 3 and a plurality of $L_2$ are mutually the same or different; and qa is an integer from 1 to 4 and a plurality of group represented by a formula (22x) below bonded to $Ar_{21}$ are mutually the same or different,

(22x)

16. The organic electroluminescence device according to claim 15, wherein
the substituted or unsubstituted fused aromatic hydrocarbon group having 10 to 30 ring carbon atoms in $Ar_{21}$ is a group derived from a fused aromatic hydrocarbon selected from the group consisting of naphthalene, anthracene, phenanthrene, fluorene, pyrene, chrysene, fluoranthene, benzo[a]anthracene, benzo[c]phenanthrene, triphenylene, benzo[g]chrysene, benzo[b]triphenylene, picene, and perylene.

17. The organic electroluminescence device according to claim 15, wherein
the substituted or unsubstituted fused aromatic hydrocarbon group having 10 to 30 ring carbon atoms in $Ar_{21}$ is a group derived from a fused aromatic hydrocarbon selected from the group consisting of phenanthrene, pyrene, chrysene, fluoranthene, triphenylene, and benzo[g]chrysene.

18. The organic electroluminescence device according to claim 15, wherein
the second compound is represented by a formula (23) below,

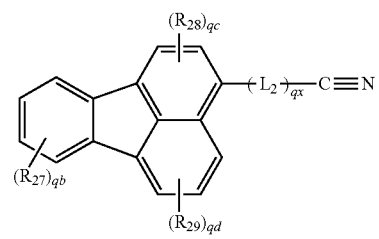

(23)

where: $L_2$ represents the same as $L_2$ in the formula (22);

$R_{27}$ to $R_{29}$ are each independently a hydrogen atom or a sub stituent, and, when $R_{27}$ to $R_{29}$ are sub stituents, each of the sub stituents is a sub stituent selected from the group consisting of a halogen atom, a hydroxyl group, a cyano group, a substituted or unsubstituted alkyl group having 1 to 30 carbon atoms, a substituted or unsubstituted alkoxy group having 1 to 30 carbon atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a silyl group represented by -Si($R_{221}$)$_3$, an amino group represented by -N($R_{222}$)$_2$, a substituted or unsubstituted aromatic hydrocarbon group having 6 to 30 ring carbon atoms, and a substituted or unsubstituted heterocyclic group having 5 to 30 ring atoms;

$R_{221}$ is each independently a hydrogen atom or a substituent, and when $R_{221}$ is a substituent, the substituent is a substituted or unsubstituted alkyl group having 1 to 30 carbon atoms, or a substituted or unsubstituted aromatic hydrocarbon group having 6 to 30 ring carbon atoms;

a plurality of $R_{221}$ are mutually the same or different;

$R_{222}$ is each independently a hydrogen atom or a substituent, and when $R_{222}$ is a substituent, the substituent is a substituted or unsubstituted alkyl group having 1 to 30 carbon atoms, or a substituted or unsubstituted aromatic hydrocarbon group having 6 to 30 ring carbon atoms;

a plurality of $R_{222}$ are mutually the same or different;

qb is 4 and a plurality of $R_{27}$ are mutually the same or different;

qc is 2 and a plurality of $R_{28}$ are mutually the same or different;

qd is 3 and a plurality of $R_{29}$ are mutually the same or different;

qx is an integer from 1 to 3 and a plurality of $L_2$ are mutually the same or different; and each of $R_{27}$ to $R_{29}$ is bonded to a carbon atom of each of the aromatic rings.

19. The organic electroluminescence device according to claim 15, wherein $L_2$ is a linking group and the linking group in $L_2$ is a substituted or unsubstituted aromatic hydrocarbon group having 6 to 30 ring carbon atoms.

20. The organic electroluminescence device according to claim 15, wherein qx is 2 or 3, and the plurality of $L_2$ are each independently selected from the group consisting of a substituted or unsubstituted aromatic hydrocarbon group having 6 to 30 ring carbon atoms.

21. The organic electroluminescence device according to claim 19, wherein $L_2$ is a phenylene group, biphenyldiyl group, or naphthylene group.

22. The organic electroluminescence device according to claim 19, wherein the linking group in $L_2$ comprises a phenylene group bonded with a cyano group at a meta position or a para position.

23. The organic electroluminescence device according to claim 1, further comprising:

an electron transporting layer between the emitting layer and the cathode.

24. The organic electroluminescence device according to claim 1, further comprising:

a hole transporting layer between the emitting layer and the anode.

25. An electronic device comprising the organic electroluminescence device according to claim 1.

26. The organic electroluminescence device according to claim 1, wherein the singlet energy S(M1) of the first compound and the singlet energy S(M2) of the second compound satisfy a relationship of Numerical Formula 4 below, the triplet energy T(M1) of the first compound and a triplet energy T(M2) of the second compound satisfy a relationship of Numerical Formula 7 below, a singlet energy S(M3) of the third compound and the singlet energy S(M1) of the first compound satisfy a relationship of Numerical Formula 12 below, and the third compound is a fluorescent material, $S(M2) \geq S(M1)$  (Numerical Formula 4)

$T(M1) < T(M2)$  (Numerical Formula 7)

$S(M1) > S(M3)$  (Numerical Formula 12).

27. The organic electroluminescence device according to claim 1, wherein the singlet energy S(M1) of the first compound and the singlet energy S(M1) of the second compound satisfy a relationship of Numerical Formula 4 below, the triplet energy T(M1) of the first compound and a triplet energy T(M2) of the second compound satisfy a relationship of Numerical Formula 7 below, a singlet energy S(M3) of the third compound and the singlet energy S(M1) of the first compound satisfy a relationship of Numerical Formula 12 below, the third compound is a fluorescent material, and the first compound is represented by a formula (1) below, $S(M2) \geq S(M1)$ tm (Numerical Formula 4)

$T(M1) < T(M2)$ tm (Numerical Formula 7)

$S(M1) > S(M3)$ tm (Numerical Formula 12)

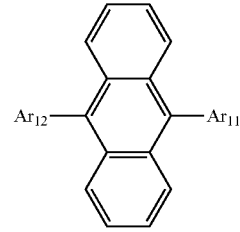

(1)

where: $Ar_{11}$ and $Ar_{12}$ are each independently a substituted or unsubstituted aromatic hydrocarbon group having 6 to 30 ring carbon atoms, or substituted or unsubstituted heterocyclic group having 5 to 30 ring atoms.

* * * * *